United States Patent
Zhang et al.

(10) Patent No.: US 10,630,917 B1
(45) Date of Patent: Apr. 21, 2020

(54) APPARATUS AND METHODS FOR ALL-CMOS COMPRESSIVE SENSING

(71) Applicant: Massachusetts Institute of Technology, Cambridge, MA (US)

(72) Inventors: Jie Zhang, Boston, MA (US); Jonathan Paul Newman, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 15 days.

(21) Appl. No.: 16/145,472

(22) Filed: Sep. 28, 2018

(51) Int. Cl.
| | |
|---|---|
| *H04N 5/353* | (2011.01) |
| *G01N 33/50* | (2006.01) |
| *H04N 5/3745* | (2011.01) |
| *H04N 5/917* | (2006.01) |
| *H04N 5/363* | (2011.01) |
| *G01N 21/64* | (2006.01) |

(52) U.S. Cl.
CPC ....... *H04N 5/3535* (2013.01); *G01N 21/6486* (2013.01); *G01N 33/5091* (2013.01); *H04N 5/363* (2013.01); *H04N 5/37452* (2013.01); *H04N 5/917* (2013.01)

(58) Field of Classification Search
CPC .. H04N 5/3535; H04N 5/37452; H04N 5/917; H04N 5/636; G01N 33/5091
See application file for complete search history.

(56) References Cited

U.S. PATENT DOCUMENTS

| | | | |
|---|---|---|---|
| 4,324,462 A | 4/1982 | Tano et al. | |
| 8,785,867 B2 | 7/2014 | Zhang et al. | |
| 2003/0103141 A1 | 6/2003 | Bechtel et al. | |
| 2004/0227828 A1* | 11/2004 | Loose | H04N 5/23225 348/294 |
| 2010/0182468 A1 | 7/2010 | Posch et al. | |
| 2014/0043486 A1* | 2/2014 | Zhai | G01N 21/763 348/163 |
| 2015/0301030 A1* | 10/2015 | Eggan | G01N 33/5058 435/29 |
| 2016/0070944 A1 | 3/2016 | McCloskey et al. | |
| 2017/0153336 A1 | 6/2017 | Kawanabe et al. | |
| 2018/0115725 A1* | 4/2018 | Zhang | H04N 5/37455 |

OTHER PUBLICATIONS

Aharon et al., "K-SVD: An algorithm for designing overcomplete dictionaries for sparse representation." IEEE Transactions on signal processing 54.11 (2006): 4311. 12 pages.

(Continued)

*Primary Examiner* — Christopher K Peterson
(74) *Attorney, Agent, or Firm* — Smith Baluch LLP

(57) ABSTRACT

An apparatus includes an array of pixels. At least a first pixel in the array of pixels includes a first detector to generate a first electrical signal in response to irradiation by incident radiation, a first transistor electrically coupled to the first detector, and at least one logic gate to implement a Boolean AND logic function. The logic gate includes a first input terminal to receive a first exposure signal, a second input terminal to receive a first reset signal, and an output terminal, electrically coupled to the first transistor, to output to the first transistor a first control signal to variably control a first variable exposure time of the first detector and to reset the first detector.

20 Claims, 21 Drawing Sheets

(56) References Cited

OTHER PUBLICATIONS

Aktakka et al., "Energy scavenging from insect flight." Journal of Micromechanics and Microengineering 21.9 (2011): 095016. 12 pages.

Akyildiz et al., "A survey on sensor networks." IEEE communications magazine 40.8 (2002): 102-114.

Bub et al., "Temporal pixel multiplexing for simultaneous high-speed, high-resolution imaging." Nature methods 7.3 (2010): 209. 5 pages.

Donoho, "Compressed sensing." IEEE Transactions on information theory 52.4 (2006): 1289-1306. 18 pages.

Duarte et al., "Single-pixel imaging via compressive sampling." IEEE signal processing magazine 25.2 (2008): 83-91.

Hitomi et al., "Video from a single coded exposure photograph using a learned over-complete dictionary." Computer Vision (ICCV), 2011 IEEE International Conference on. IEEE, 2011. 8 pages.

Koller et al., "High spatio-temporal resolution video with compressed sensing." Opt. Express 23.12 (2015): 15992-16007. 16 pages.

Li et al., "A framework of mixed sparse representations for remote sensing images." IEEE Transactions on Geoscience and Remote Sensing 55.2 (2017): 1210-1221.

Li et al., "Coded-exposure camera and its circuits design." Cluster Computing 20.4 (2017): 3003-3014.

Li et al., "High efficient optical remote sensing images acquisition for nano-satellite-framework." Sensors, Systems, and Next-Generation Satellites XXI. vol. 10423. International Society for Optics and Photonics, 2017.13 pages.

Li et al., "Joint structural similarity and entropy estimation for coded-exposure image restoration." Multimedia Tools and Applications (2018): 1-18.

Lin et al., "Dual-coded compressive hyperspectral imaging." Optics letters 39.7 (2014): 2044-2047.

Liu et al., "Efficient space-time sampling with pixel-wise coded exposure for high-speed imaging." IEEE transactions on pattern analysis and machine intelligence 36.2 (2014): 248-260.

Liu et al., "Observation range-based compressive sensing and its application in TOA estimation with low-flux pulsars." Optik—International Journal for Light and Electron Optics 148 (2017): 256-267.

Llull et al., "Coded aperture compressive temporal imaging." Optics express 21.9 (2013): 10526-10545. 20 pages.

Luo et al., "A CMOS pixel design with binary space-time exposure encoding for computational imaging." Custom Integrated Circuits Conference (CICC), 2017 IEEE. IEEE, 2017. 4 pages.

Luo et al., "Always-on CMOS image sensor pixel design for pixel-wise binary coded exposure." Circuits and Systems (ISCAS), 2017 IEEE International Symposium on. IEEE, 2017. 4 pages.

Luo et al., "Exposure-Programmable CMOS Pixel With Selective Charge Storage and Code Memory for Computational Imaging." IEEE Transactions on Circuits and Systems I: Regular Papers 65.5 (2018): 1555-1566.

Mochizuki et al., "6.4 Single-shot 200Mfps 5× 3-aperture compressive CMOS imager." Solid-State Circuits Conference—(ISSCC), 2015 IEEE International. IEEE, 2015. 3 pages.

Oike et al., "CMOS image sensor with per-column ?? ADC and programmable compressed sensing." IEEE Journal of Solid-State Circuits 48.1 (2013): 318-328.

Raskar et al., "Coded exposure photography: motion deblurring using fluttered shutter." ACM Transactions on Graphics (TOG) 25.3 (2006): 795-804.

Sayilir et al., "A-90 dBm sensitivity wireless transceiver using VCO-PA-LNA-switch-modulator co-design for low power insect-based wireless sensor networks." IEEE Journal of Solid-State Circuits 49.4 (2014): 996-1006.

Tang et al., "Motion deblurring based on local temporal compressive sensing for remote sensing image." Optical Engineering 55.9 (2016): 093106. 12 pages.

Thomas et al., "A battery-free multichannel digital neural/EMG telemetry system for flying insects." IEEE transactions on biomedical circuits and systems 6.5 (2012): 424-436.

Tsai et al., "Spatial light modulator based color polarization imaging." Optics express23.9 (2015): 11912-11926.

Tsai et al., "Spectral-temporal compressive imaging." Optics letters 40.17 (2015): 4054-4057.

Wang et al., "Using Deep Learning to Extract Scenery Information in Real Time Spatiotemporal Compressed Sensing." Circuits and Systems (ISCAS), 2018 IEEE International Symposium on. IEEE, 2018. 4 pages.

Wei et al., "Coded Two-Bucket Cameras for Computer Vision." Proceedings of the European Conference on Computer Vision (ECCV). 2018. pp. 54-71.

White et al., "Contaminant cloud boundary monitoring using network of UAV sensors." IEEE Sensors Journal 8.10 (2008): 1681-1692.

Xiong et al., "Live demonstration: A compact all-CMOS spatiotemporal compressed sensing video camera." Circuits and Systems (ISCAS), 2017 IEEE International Symposium on. IEEE, 2017. 1 page.

Xiong, Data-Driven Representation, Learning and Applications: From Compressed Sensing to Deep Neural Networks Diss. Johns Hopkins University, 2017. 199 pages.

Yu et al., "Miniaturized optical neuroimaging in unrestrained animals." NeuroImage 113 (2015): 397-406.

Yuan et al., "Compressive hyperspectral imaging with side information." IEEE Journal of Selected Topics in Signal Processing 9.6 (2015): 964-976.

Zhang et al., "Cmos implementation of pixel-wise coded exposure imaging for insect-based sensor node." Biomedical Circuits and Systems Conference (BioCAS), 2015 IEEE. IEEE, 2015. 4 pages.

Zhang et al.,"Compact all-CMOS spatiotemporal compressive sensing video camera with pixel-wise coded exposure." Optics express 24.8 (2016): 9013-9024.

Liu et al. "High efficient optical remote sensing images acquisition for nano-satellite: reconstruction algorithms." Image and Signal Processing for Remote Sensing XXIII. vol. 10427. International Society for Optics and Photonics, 2017. 13 pages.

International Search Report and Written Opinion in International Patent Application No. PCT/US2019/053258 dated Dec. 31, 2019, 13 pages.

Sarhangnejad et al., Dual-Tap Pipelined-Code-Memory Coded-Exposure-Pixel CMOS Image Sensor for Multi-Exposure Single-Frame Computational Imaging. IIEEE International Solid-State Circuits Conference, Feb. 2019.

* cited by examiner

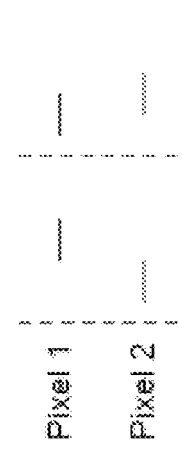
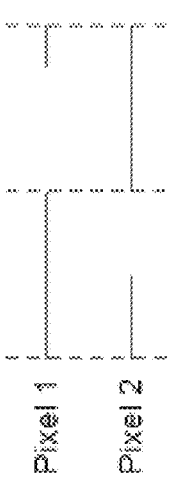
FIG. 5A  FIG. 5B  FIG. 5C  FIG. 5D

APPARATUS AND METHODS FOR ALL-CMOS COMPRESSIVE SENSING

BACKGROUND

The performance of conventional CMOS Image Sensor (CIS) is usually subject to a tradeoff between the signal-to-noise ratio (SNR) and the frame rate, both of which are directly linked to the exposure time as used in image taking. On the one hand, short exposure time allows a high frame rate and can be employed to capture fast motions, but this also leads to a low pixel SNR at low light intensity. On the other hand, long exposure time can improve pixel SNR but usually induce motion blurring in the resulting images and photodiode well saturation.

A number of computational imaging methods have been developed to address these tradeoffs. One example is the pixel-wise exposure using a digital micro-mirror device (DMD). With controlled exposure, the resulting system can operate at a slow frame rate with better SNR and dynamic range for high-speed imaging tasks. Another example is the flutter shutter technique, which can reduce motion blurring by exposing the pixels using a temporally coded shutter, instead of a continuous exposure. The added pattern can improve invertibility of the blur matrix, thereby increasing the ability to de-wrap a blurred image.

Inspired by the theory of Compressed Sensing (CS), a number of CS-based imaging techniques also emerged to improve spatial and temporal resolution of image sensors. Existing CS-based sensors use optical frontend to apply a random pixel wise exposure pattern to the focal plane of the sensor. The image sensor then samples the modulated video. These methods compress a spatiotemporal video into a single image. Using inherent sparsity in natural scenes, the video can be then recovered from the compressed image using optimization algorithms.

Previous temporal CS imaging systems have demonstrated high image quality at high reconstruction frame rate. But all the previous implementations (both CS based and non-CS based) use optical apparatus to pre-modulate the video scene before the image sensor. For example, optical exposure control can use off-chip spatial light modulators (SLM), such as digital micro-mirror devices (DMD) or liquid-crystal-on-silicon (LCOS) devices, to modulate pixel exposure prior to the sensor focal plane. Using different spatiotemporal optical masks, exposure-coded imaging can capture blur-free motion at a slow frame rate. However, the opto-mechanical apparatus for optical exposure control increases the overall system size and power consumption, thereby limiting the potential of the resulting system to be further miniaturized.

SUMMARY

Embodiments of the present technology generally relate to compressive sensing. In one example, an apparatus includes an array of pixels. At least a first pixel in the array of pixels includes a first detector to generate a first electrical signal in response to irradiation by incident radiation, a first transistor electrically coupled to the first detector, and at least one logic gate to implement a Boolean AND logic function. The logic gate includes a first input terminal to receive a first exposure signal, a second input terminal to receive a first reset signal, and an output terminal, electrically coupled to the first transistor, to output to the first transistor a first control signal to variably control a first variable exposure time of the first detector and to reset the first detector.

In another example, a method of compressive sensing is performed using an array of pixels. Each pixel in the array of pixels includes a detector and at least one logic gate implementing a Boolean AND function and having a first input terminal, a second input terminal, and an output terminal electrically coupled to the detector. The method includes, for each pixel of at least a first group of pixels in the array of pixels, sending an exposure signal, generated by a random generator, to the first input terminal of the at least one logic gate. The method also includes sending a reset signal to the second input terminal of the at least one logic gate and generating an electrical signal representative of a scene, in response to irradiation of the detector by incident photons emitted from the scene, based on an output signal of the at least one logic gate. The output signal variably controls a variable exposure time of the detector and resetting the detector.

In yet another example, an apparatus for compressive sensing includes an array of pixels having M rows of pixels and N columns of pixels. Each pixel in the array of pixels includes a photodiode to generate an electrical signal in response to irradiation by incident radiation, a first transistor electrically coupled to the photodiode, and a logic gate implementing a Boolean AND logic function. The logic gate includes a first input terminal to receive a first exposure signal, a second input terminal to receive a first reset signal, and an output terminal, electrically coupled to the first transistor, to output to the first transistor a first control signal controlling a variable exposure time of the photodiode and resetting the photodiode. The apparatus also includes memory, operably coupled to the array of pixels, to store a plurality of exposure signals including the first exposure signal. The apparatus also includes a memory interface, operably coupled to the memory and the array of pixels, to transmit an ith exposure signal to an ith column of pixels, where i=1, 2, ... N. A random generator is operably coupled to the memory to generate the plurality of exposure signals. A first exposure signal includes a first sequence of valleys distributed within a predetermined time span and a second exposure signal includes a second sequence of valleys distributed within the predetermined time span.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 5A-5D illustrate a variety of exemplary exposure periods for two pixels over two frames in STCS.

DETAILED DESCRIPTION

Overview of Compressive Sensing Pixel-Wise Coded Exposure (CS-PCE)

Figure 1A:
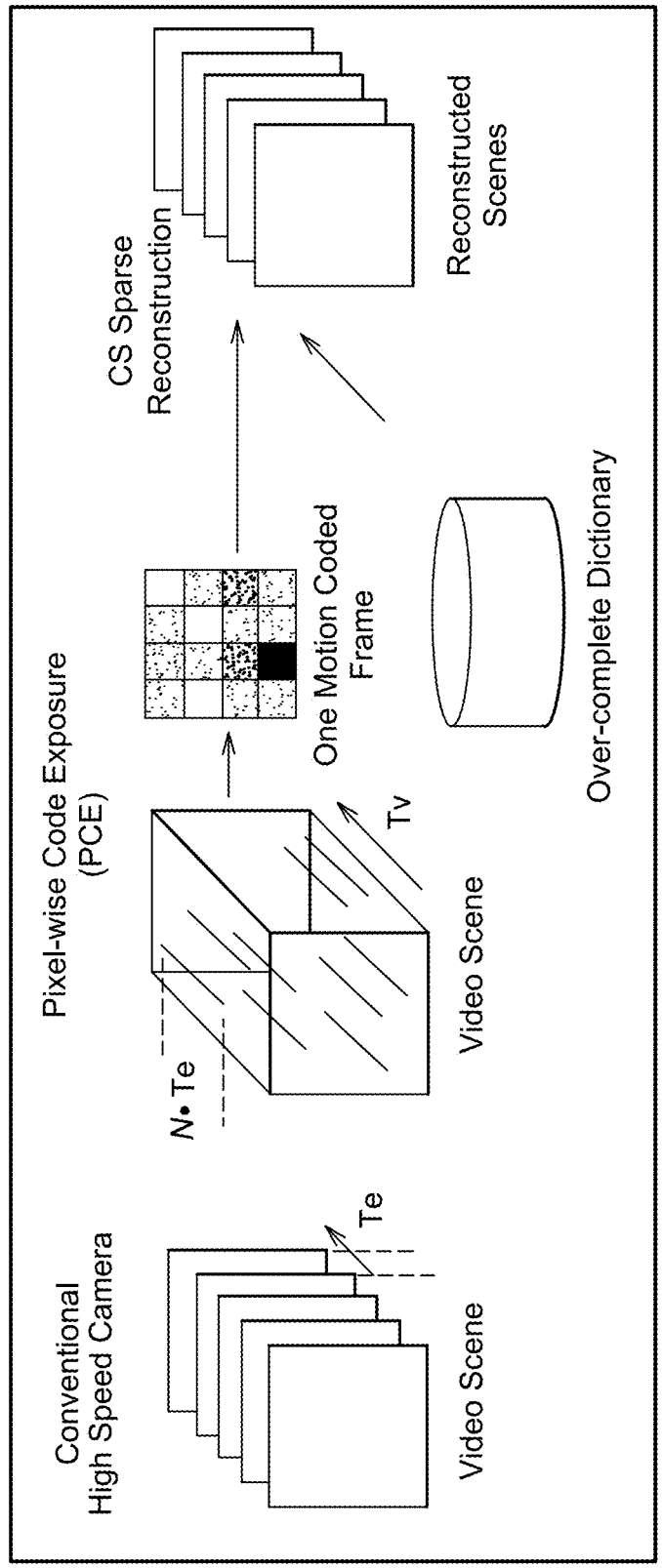
FIGS. 1A and 1B illustrate the principles of compressive sensing.
Figure 1B:
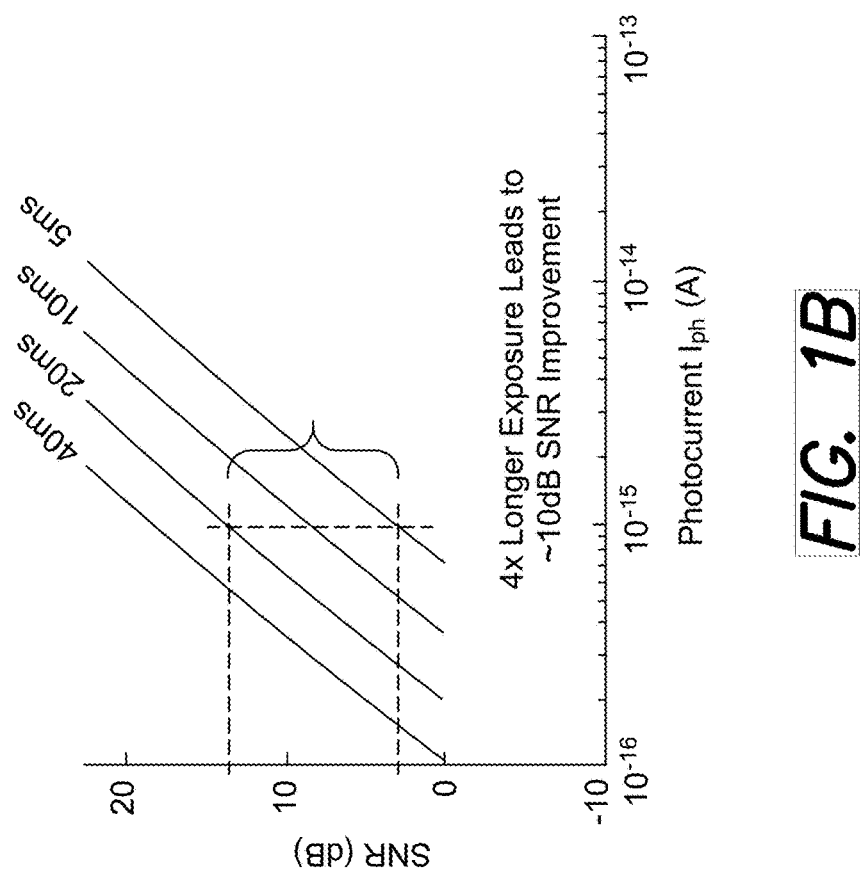

To address the challenges in conventional compressing sensing, apparatus, systems, and methods employ a Compressive Sensing Pixel-Wise Coded Exposure (CS-PCE) technique. FIGS. 1A and 1B illustrate the principles of CS-PCE. FIG. 1A shows the difference between a conventional high speed camera and the CS Pixel-wise Coded Exposure (CS-PCE) technique. In a conventional high speed camera, all pixels are exposed for a fixed amount of time $T_e$, which is determined by the frame rate. Usually, compression is performed after global sampling and storage (e.g., compression through JPEG standard). Global sampling can generate large amounts of unnecessary data while limiting pixel signal-to-noise ratio (SNR) due to extremely short exposure (e.g., about 1 ms for a 1000 FPS camera).

In the CS-PCE technique, pixels are exposed through a random, "single-on" exposure of fixed duration at multiples of Te (i.e., NTe, where N is a positive integer) within a longer temporal duration of Tv. The readout circuit in CS-PCE samples the pixel value at the end of Tv with a readout speed of 1/Tv. PCE essentially compresses a spatiotemporal video into a single coded image. Upon receiving the coded image, PCE reconstructs the entire video from the single coded image using sparse spatiotemporal reconstruction with an over-complete dictionary. Since the reconstructed framerate is 1/(unit time of Te), PCE can provide a high frame rate using the same readout speed as a conventional image sensor.

PCE is also different from traditional spatial CS approach, which recovers one frame using multiple random spatial samples. Thus, PCE is more suitable for video applications because the sparse samples include both spatial and temporal information. Previous work using optical implementations have shown that PCE is capable of extracting low blur videos from dynamic scenes with occlusions, deforming objects, gas and liquid flow.

Another advantage of CS-PCE is that CS-PCE allows longer pixel exposure time across multiple frames. Image SNR usually improves with longer exposure time, as illustrated in FIG. 1B. For example, applying this to genetically encoded voltage indicator (GEVI) imaging, a 1000 FPS sCMOS camera is limited to Te=1 ms exposure time, thereby resulting in frames with a low SNR. With 4× longer exposure (i.e., NVTe=4 ms) in CS-PCE, the coded image can be sampled with at least 10 dB SNR improvement. This relaxes the noise and sensitivity constraints of the CMOS pixel and also improves the detectability of the GEVI indicators.

Reconstructions of images acquired via CS-PCE can be illustrated mathematically. In one embodiment, to determine the reconstructed video scene, an optimal video corresponding to the coded image is determined by solving an inverse problem using an over-complete dictionary. For example, let there be spatiotemporal video scene $X \in \mathbb{R}^{M \times N \times T}$ where M×N indicates the size of each frame, T indicates the total number of frames in the video and X(m, n, t) is the pixel value associated with frame t at position (m,n). A sensing cube, $S \in \mathbb{R}^{M \times N \times T}$ stores exposure control values for pixels at (m, n, t). The value of S(m, n, t) is 1 for frames $t \in [t_{start}, t_{end}]$ and 0 otherwise, where $[t_{start}, t_{end}]$ denotes the start and end frame numbers for a particular pixel. For compressed sensing, start is $t_{start}$ randomly chosen for every pixel and is based on the exposure-control bits in the random exposure sequence, while exposure duration is fixed.

To acquire a coded image, $Y \in \mathbb{R}^{M \times N \times T}$, video X is modulated by the S before projection across multiple temporal frames. The value of a pixel Y at location (m, n) is computed as:

$$Y(m,n) = \Sigma_{t=1}^{T} S(m,n,t) \cdot X(m,n,t) \tag{1}$$

During reconstruction, the reconstructed spatiotemporal video, $\hat{X} \in \mathbb{R}^{M \times N \times T}$ can be recovered by solving:

$$\hat{X} = \mathrm{argmin}_a \|a\|_0 \text{ s.t. } \|Y - SDa\|_2 \leq \varepsilon \tag{2}$$

where $D \in \mathbb{R}^{M \times N \times T \times L}$ is the over-complete dictionary. M×N×T denotes the dimension of the single spatiotemporal dictionary item and L denotes the overall size of the dictionary. $a \in \mathbb{R}^L$ is the sparse representation of X using the dictionary D. ε is the tolerable reconstruction error. Further, a learning algorithm such as the K-SVD algorithm can be used for the dictionary learning. Other dictionary methods can be used as well.

In some embodiments, to reconstruct a video from the global exposure fame, a block-wise approach can be implemented. In this approach, the coded image from the global exposure frame is broken down into blocks. A spatiotemporal cube can then be reconstructed by using a dictionary. In one specific example, the coded image is broken down into an 8×8 segment and a spatiotemporal cube with parameters of 8×8×14 can be reconstructed using a dictionary. The dictionary may have a size of 896×3000 parameters, but in various embodiments, the size of the dictionary can vary and be based on at least one of the output FPS, the features of the video frame, and number of pixels in the scene capture device. The coded image can be segmented into different size blocks and dictionaries of different sizes can be used to generate a spatiotemporal cube of different sizes. The reconstructed video scene can be stored to a memory of a computer system and/or displayed on a display of a computer system.

The dictionary can be trained based on data from various objects and movement at a desired output frame rate. For example, the dictionary can be trained based on data at a rate of 100 FPS. Further, a K-SVD algorithm may be used to train the dictionary based on the data. Other algorithms may also be used. In one embodiment, the dictionary can be referred to as an over-complete dictionary. The dictionary training is a method to extract features of the video for sparse encoding. The dictionary items contain moving surfaces and edges that are building blocks of videos. Therefore, the dictionary can be generalized. For example, a dictionary trained using natural videos can be used to reconstruction fluorescent signals in in vivo imaging of genetically encoded calcium indictors in cells.

Apparatus for Implementing CS-PCE

Figure 2A:
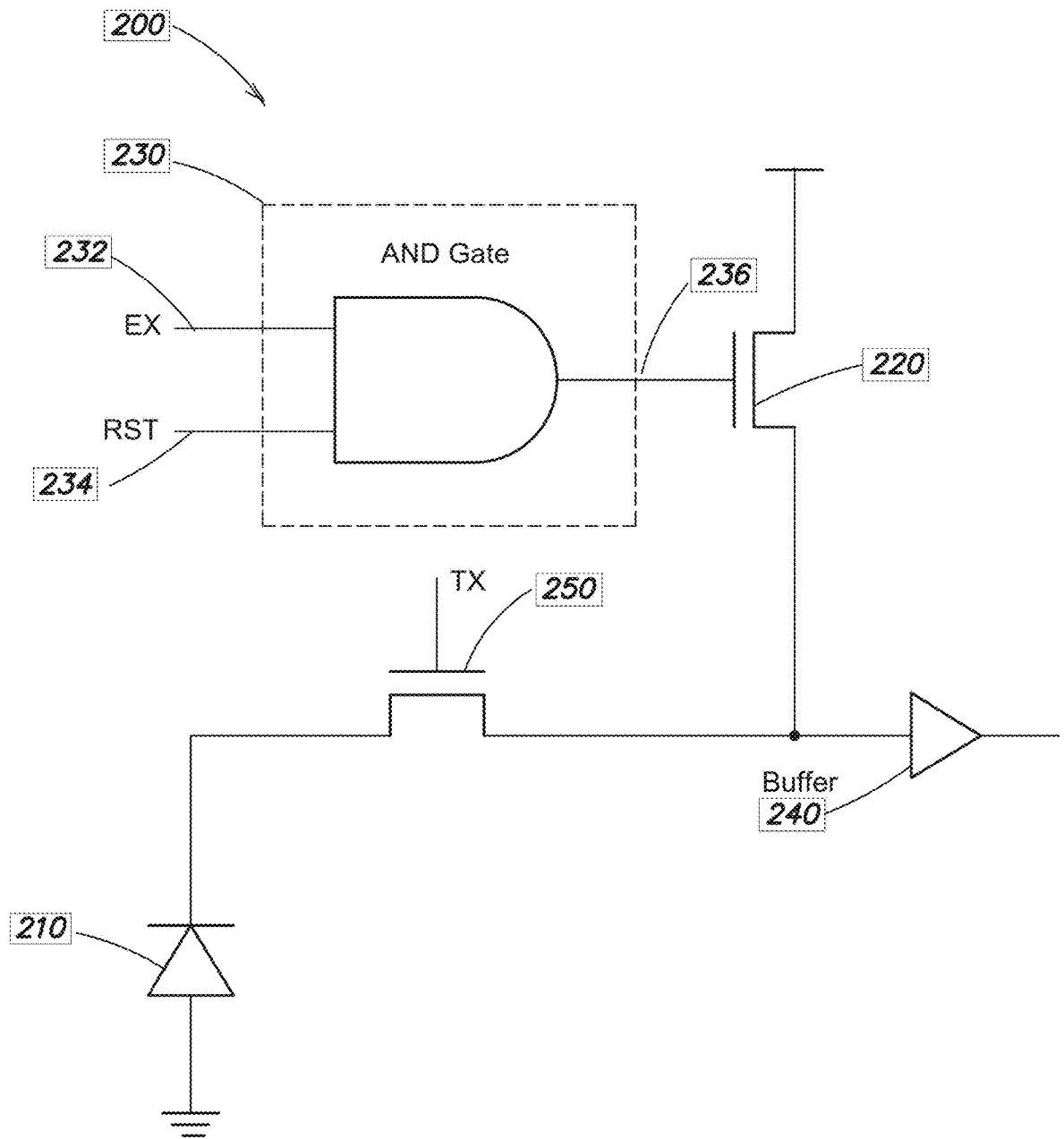
FIG. 2A shows a schematic of an apparatus for compressive sensing.

FIG. 2A shows a schematic of an apparatus 200 to implement the CS-PCE technique described herein. The apparatus 200 has a semiconductor architecture that can be smaller and more power-efficient than a comparable optical system. In one embodiment, the semiconductor process is a CMOS process. Through the use of in-pixel memory (optional) and circuit-reset-modulation technique, the apparatus 200 can implement on-chip exposure control without using additional optical elements. Overall, the semiconductor implementation can reduce the size and power, expanding the application of the PCE technique to small low power sensing devices.

In some examples, the apparatus 200 can be configured as a pixel in an array of pixels for imaging (see, e.g., FIG. 11 below). A detector 210 (e.g., a photodiode) is employed to generate an electrical signal in response to irradiation by incident radiation. The detector 210 is electrically coupled to a first transistor 220, which in turn is electrically coupled to a logic gate 230 that implements a Boolean AND logic function. The logic gate 230 includes a first input terminal 232 to receive an exposure signal (i.e. EX), a second input terminal 234 to receive a reset signal (i.e. RST), and an output terminal that is electrically coupled to the first transistor 220. The output of the first transistor 220 is configured as a control signal to variably control the exposure time of the detector 210 and to reset the detector 210.

In operation, the exposure time of the detector 210 can be controlled by the combination of the exposure signal and the reset signal. More specifically, the exposure signal and the reset signal control when the exposure of the detector 210 starts and stops by preventing the pixel from being reset.

The apparatus 200 shown in FIG. 2A also includes a buffer 240 that can isolate the detector 210 from other readout circuits and circuit elements. The apparatus 200 also includes a second transistor 250 controlled by a TX signal. The second transistor 250 can act as a switch for an optional embodiment employing correlated double sampling that can be used to reduce pixel-reset noise. In some examples, the apparatus 200 can include a memory element (not shown in FIG. 2A) that is configured to store a control bit, which can be used to generate the exposure signal. The memory element can include, for example, a static random access memory (SRAM) block. Furthermore, the memory element can be a 1-bit memory. In some other examples, the array of pixels can share a memory unit (see, e.g., FIG. 11 below).

Figure 2B:
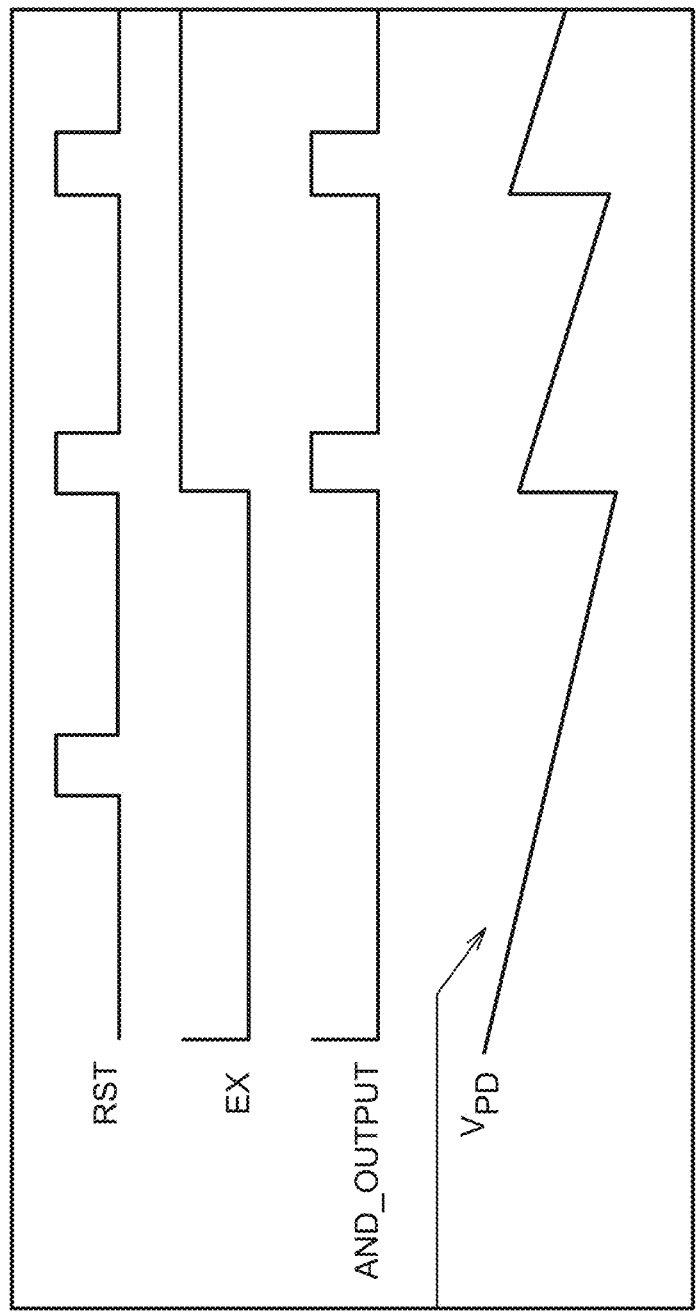
FIG. 2B illustrates an example timing diagram for operating the apparatus 200 shown in FIG. 2A.

FIG. 2B illustrates an example timing diagram for operating the apparatus 200 shown in FIG. 2A. The "EX" signal corresponds to the signal delivered into the apparatus 200 via the first input terminal 232 and the "RST" signal corresponds to signal delivered into the apparatus 200 via the second input terminal 234. "AND_OUTPUT" refers to the output signal delivered by the output terminal 236. "$V_{PD}$" refers to the voltage on the detector 210. The AND gate's output is high only when both EX and RST are high. Therefore, when a row in a chip made of pixels like the apparatus 200 need to be continuously exposed, the EX signal can drop low. This can keep the output of the AND gate to be '0' despite the value of the RST signal. Patterns of EX signal can be stored inside an on-chip RAM to be read in during readout. Compared with the situation where the EX signal is applied to the detector 210 via a separate transistor (i.e., separate from the transistor 220), using the AND gate 230 has the advantage of lower dark current.

As illustrated in FIG. 2B, when the EX signal is high, the RST signal resets the voltage of the detector 210 at the beginning of each frame within the video frame. When the EX signal is low, the voltage on the detector 210 is isolated from the input of the buffer 240 and $V_{PD}$ continues to discharge regardless of the state of the RST signal. The exposure period ends for the detector 210 when the EX signal is back to high level. By controlling at what points the EX signal is set high/low, the exposure timing of the detector 210 can be precisely determined.

Figure 3C:
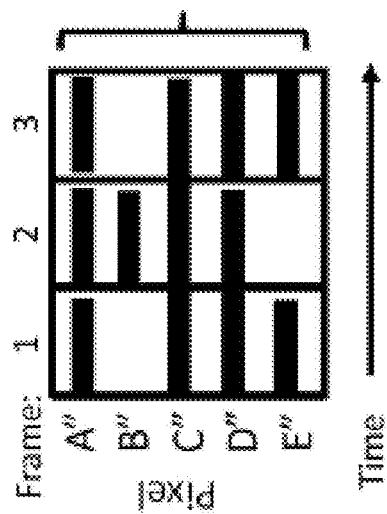
FIGS. 3A-3C illustrate exposures controls in frame-based CIS, optical-based exposure coding, and CS-PCE described herein, respectively.
Figure 3B:
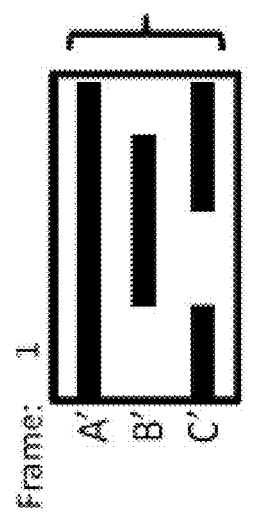
Figure 3A:
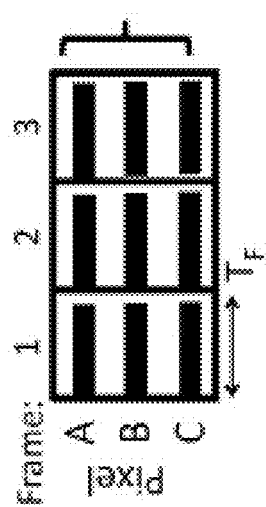

FIGS. 3A-3C illustrate exposures controls in frame-based CIS, optical-based exposure coding, and CS-PCE described herein, respectively. In a frame-based CIS, exposure control is typically controlled globally for all the pixels with pre-determined line addressing timing, as illustrated in Pixels A, B, and C in FIG. 3A. Because a pixel is typically reset before the start of the next frame, a pixels' maximum exposure time is bounded by the frame duration, $T_F$.

Compared to the electronic exposure control, optical-exposure-coded imaging can achieve flexible pixel-wise exposure, illustrated by pixels A", B", and C" in FIG. 3B. To achieve this, a spatial light modulator (SLM) can be inserted between the objective lens and image sensor focal plane to modulate the light prior to the sensor. Within one frame, the pixel value from multiple-on exposures such as pixel C" can be summed when the pixel is sampled at the end of a frame. However, despite the pixel-wise exposure flexibility, the frame rate of the camera system is still limited by the longest exposure time.

In CS-PCE described herein, the readout and exposure is independently configured for every pixel (e.g., pixels A"-E"). In addition, a pixel's exposure is no longer bounded by the frame duration and, instead, can be exposed for a multiples of the unit exposure time determined by the maximum readout speed, as illustrated by pixels C"-E" in FIG. 3C. In this technique, an analog to digital converter (ADC) only samples the pixel at the end of its exposure. Note in D", the pixel is sampled at the end of the first exposure before a second exposure takes place.

Figure 4:
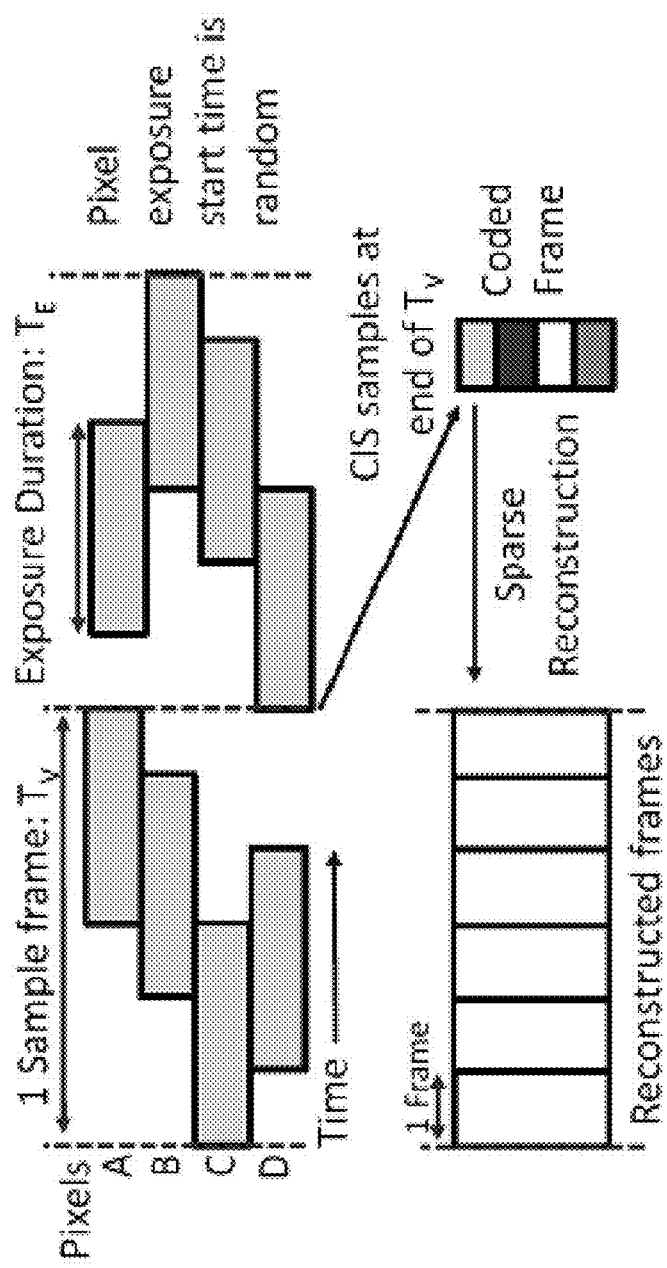
FIG. 4 illustrates spatio-temporal compressed sensing (STCS) that can be implemented by the apparatus shown in FIG. 2A.

FIG. 4 illustrates spatio-temporal compressed sensing (STCS) that can be implemented by the apparatus 200 shown in FIG. 2A. STCS is a computational imaging method to capture high frame rate video using a low frame readout rate. This method can preserve both the spatial and temporal resolution of the video. FIG. 4 illustrates the STCS acquisition flow. In STCS, pixels are exposed through a random single exposure of fixed duration $T_E$ within $T_V$, the spatio-temporal space of the video. The image sensor only reads out the pixel value at the end of $T_V$ with readout frame rate of $1/T_V$. STCS essentially compresses a video of duration $T_V$ into a single coded frame. In one embodiment, the STCS recovery algorithm reconstructs the entire video from this single coded frame using sparse spatio-temporal reconstruction with a spatial temporal dictionary. In another embodiment, the STCS recovers the video from single code frame using an over-complete dictionary. Assuming N frames are reconstructed from a single coded frame, the compression rate would be N. STCS is also different from the traditional spatial CS approach, which recovers one frame using multiple random spatial samples. Thus, STCS is more suitable for video applications because the sparse samples include both spatial and temporal information.

FIGS. 5A-5D illustrate a variety of exemplary exposure periods for two pixels over two frames in STCS. For STCS, each pixel of scene-capture device can have an exposure period that can vary from video frame to video frame. In FIGS. 5A-5D, $T_V$ denotes the frame length, while $T_E$ represents the exposure duration. In one embodiment, the exposure frames have a fixed duration, but vary when they start and stop during video frames. In another embodiment, the exposure frames have a variable duration. In one specific example, pixel 1 can have a first exposure period during a first video frame and a second exposure period during a second video frame, where the first and second exposure periods are different. The first and second exposure periods can start at different points of each video frame.

Further, in another example (see, e.g., FIG. 5B), pixel 1 has a first exposure period and pixel 2 has a second exposure period during a first video frame, where the first and second exposure periods differ. The first and second exposure periods can differ such that they start and stop at different points within the video frame, having a fixed exposure period. In other example embodiments, the exposure period differs between each pixel. As is used above, in various embodiments, a row of pixels can refer to one or more pixels that are aligned along a common row of the pixel array. In another embodiment, a row of pixels can refer to any grouping of pixels that are selected for readout at during a common period. The pixels can be grouped in any order such that each pixel is exposed and read out during a video frame.

Embodiments of the invention can also implement a local on-chip random-exposure pattern generator (REPG) dedicated to generate single-on random exposure patterns for compressed sensing applications. As described herein, in one exemplary single-on random exposure measure, each pixel is exposed only once for a duration of $T_E$ within $T_V$. The starting time of the single-on exposure can be random, as shown in FIG. 4 and FIGS. 5A-5D. More information about STCS can be found in U.S. Patent Application Publication No. 20180115725A1, entitled "Flexible pixel-wise exposure control and readout", which is incorporated herein in its entirety.

Implementing CS-PCE in Low Light Conditions

Figure 6A:
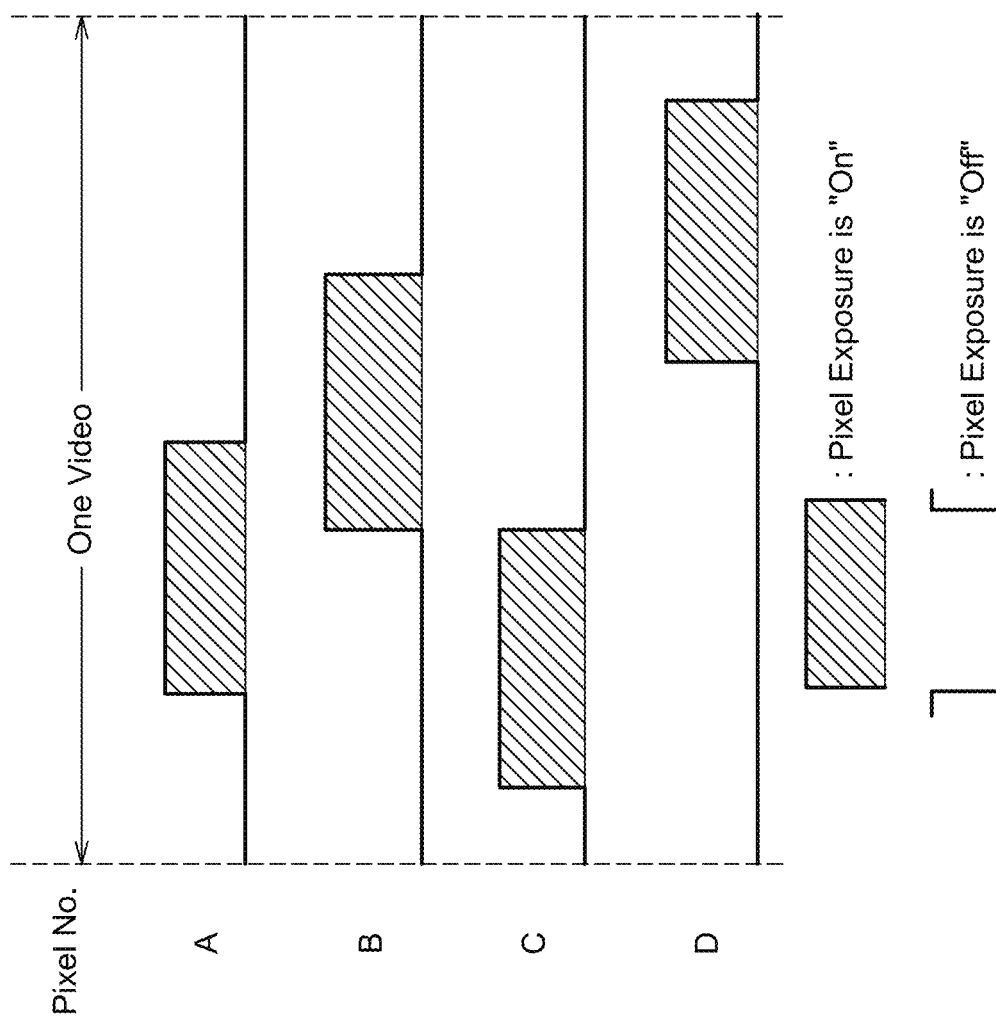
FIGS. 6A and 6B illustrate the implementation of CS-PCE in low light conditions.
Figure 6B:
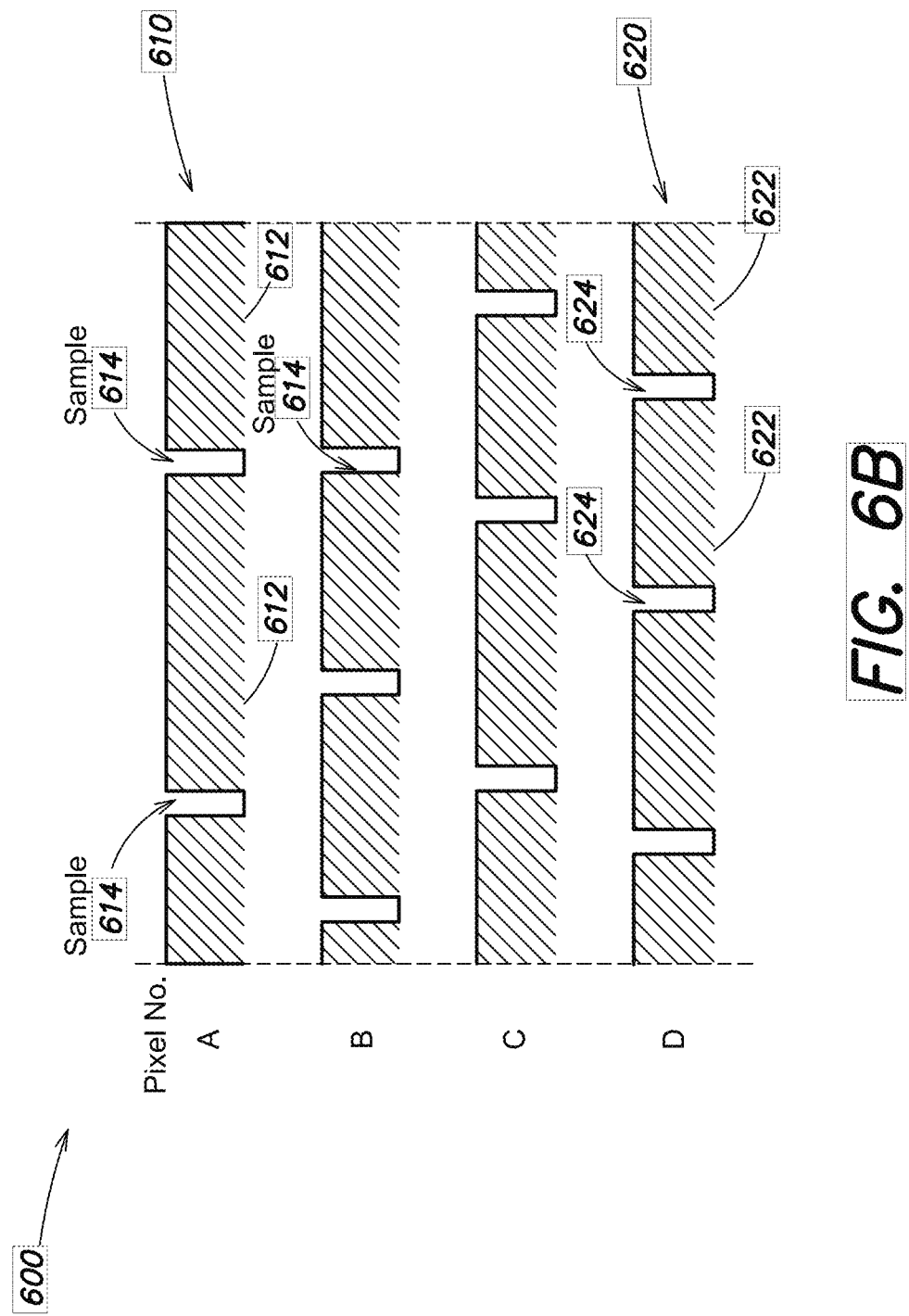

FIGS. 6A and 6B illustrate the implementation of CS-PCE in low light conditions. Without being bound by any particular theory or mode of operation, low light condition as used herein can be defined in at least two ways. In one example, the low light condition refers to conditions having empirical low brightness, in which case emitted photon counts per molecule are under certain well-defined excitation condition. For bright fluorophores under standard imaging conditions, this is on the order of about $10^4$ counts/ (moleculex second). For weak indicators, it is in the range of about tens to hundreds of counts/(moleculex second). It is worth noting that even "bright" fluorophores can still be in the category of very low light imaging compared to, e.g., daytime video.

In another example, the low light condition refers to low fluorescent efficiency. In this instance, the fraction of emitted photons to excitation photons is low, determined by the fluorescent molecules' molar extinction coefficient×quantum yield×the number of molecules in the imaging plane. For very good fluorophores, the efficiency is about $10^{-4}$. For weak ones, the efficiency can be as low as about $10^{-8}$.

FIG. 6A shows a timing diagram for CS-PCE techniques described above. Within one video, each pixel (e.g., pixels A, B, C, and D) has certain amount of "dead time" during which pixel exposure is OFF. In other words, photons are not captured during this dead time, thereby creating wasted photons. Such waste can be a challenge in low light conditions, where the number of available photons for imaging is already small.

FIG. 6B shows a timing diagram 600 (also referred to as a coded exposure pattern 600) for CS-PCE implemented in low light conditions. The diagram 600 illustrates four pixels A, B, C, and D, and the timing diagrams 610 and 620 for pixels A and D, respectively, are discussed for illustrating purposes. The timing diagram 610 for pixel A includes a plurality of exposure regions 612 separated by short gaps 614 (also referred to as intervals 614). The intervals 614 is the time to transfer charge from the photodiode to the sampling circuitry and to reset to the pixel. In some examples, the intervals 614 can be substantially equal to or less than about 1 μs (e.g., about 1 μs, about 500 ns, about 300 ns, about 200 ns, about 100 ns, or less, including any values and sub ranges in between). Similarly, the timing diagram 620 for pixel D includes a plurality of exposure regions 622 separated by short intervals 624. One difference between the two timing diagrams 610 and 620 are the locations of the intervals 614 and 624. In some examples, the intervals 614 (or 624) are randomly distributed. In some examples, the locations of intervals for one pixel is different from the locations of intervals for any other pixel in a pixel array. In other words, one difference between the pixel exposure patterns as shown in FIG. 6B are the locations of the sampling intervals. These can be randomly distributed for each pixel. Additionally, the time between adjacent intervals can be different for each pixel. For instance, in the exposure patterns 610 and 622, the locations of the sampling intervals 614 in exposure pattern 610 can be different than the sampling intervals 624 of the exposure pattern 622. In addition, the exposure times 612 of the pattern 610 are longer than the exposure times 622 of the pattern 620.

In operation, after a pixel ends its exposure, the pixel gets sampled and then gets turn on again to start the next exposure. For example, pixel A is exposed to light during one exposure region 612 and then sampled during the interval 614 immediately after the exposure region 612, followed by second exposure. This pattern 600 can significantly reduce the dead time where photons are not collected and sampled. For example, the dead time for pixel A only includes the time in the intervals 614. As a result, using the exposure pattern 600 can capture multiple coded images from a single spatio-temporal video. CS reconstruction algorithm can also benefit from having multiple samples of the same spatio-temporal video.

Figure 7:
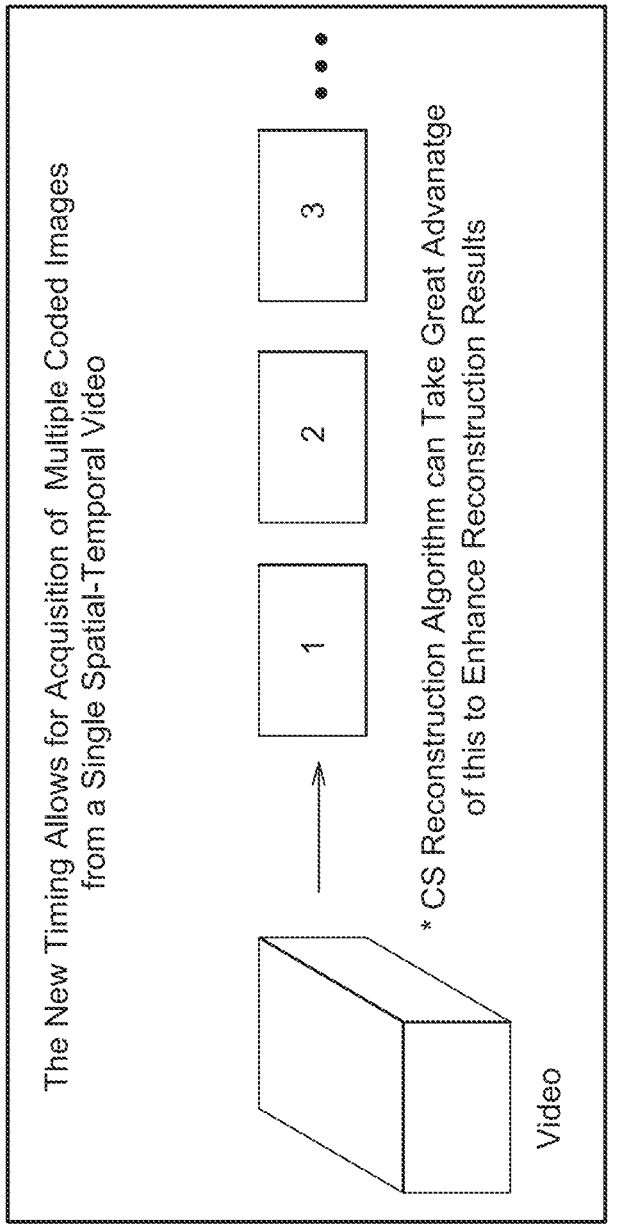
FIG. 7 illustrates the advantage of the sampling pattern shown in FIG. 6B.

FIG. 7 illustrates the advantage of the sampling pattern 600 shown in FIG. 6B. The sampling pattern 600 allows the acquisition of multiple coded images from a single spatio-temporal video. CS reconstruction algorithm can take great advantage of this to enhance reconstruction quality (e.g., high SNR as discussed below).

Figure 8A:
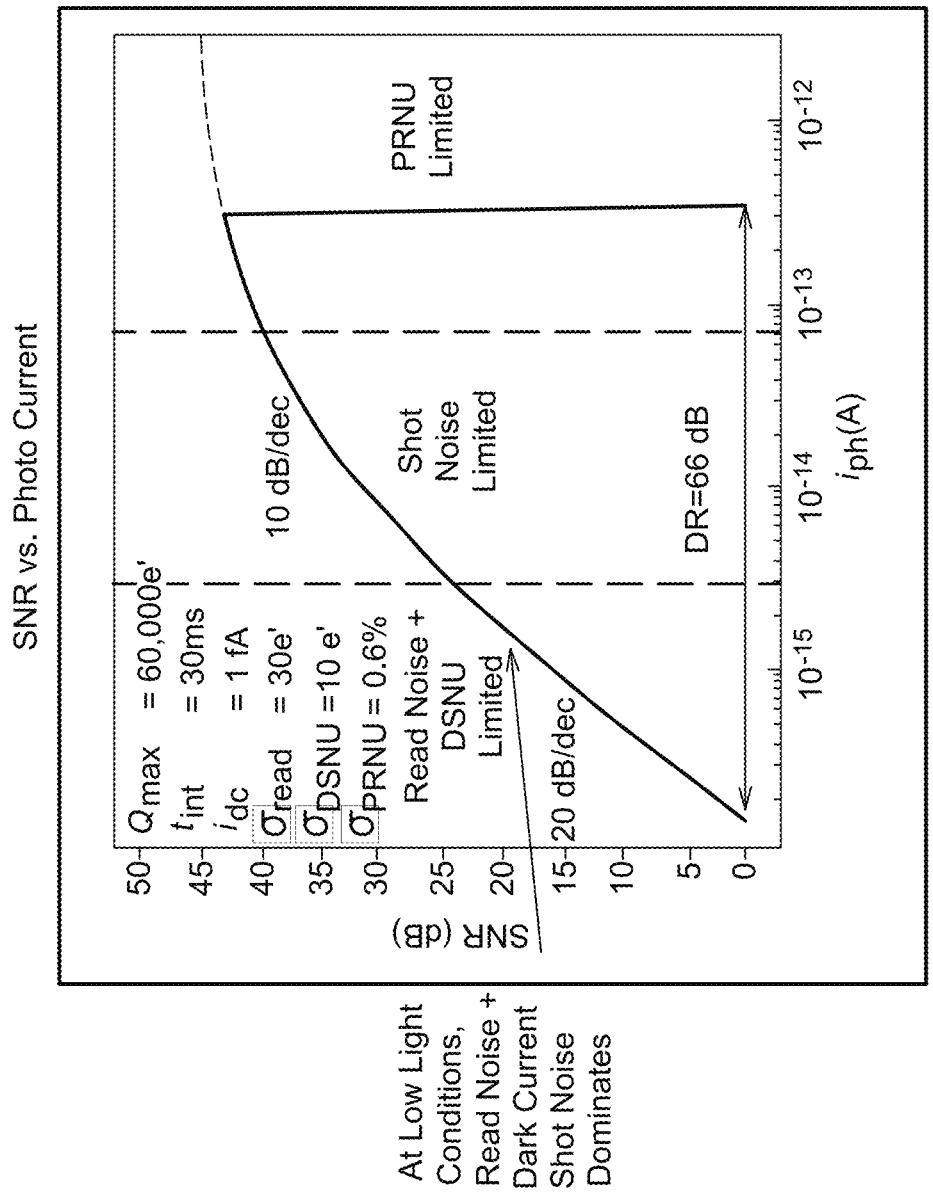
FIG. 8A shows dominant noise source at different photocurrent.
Figure 8B:
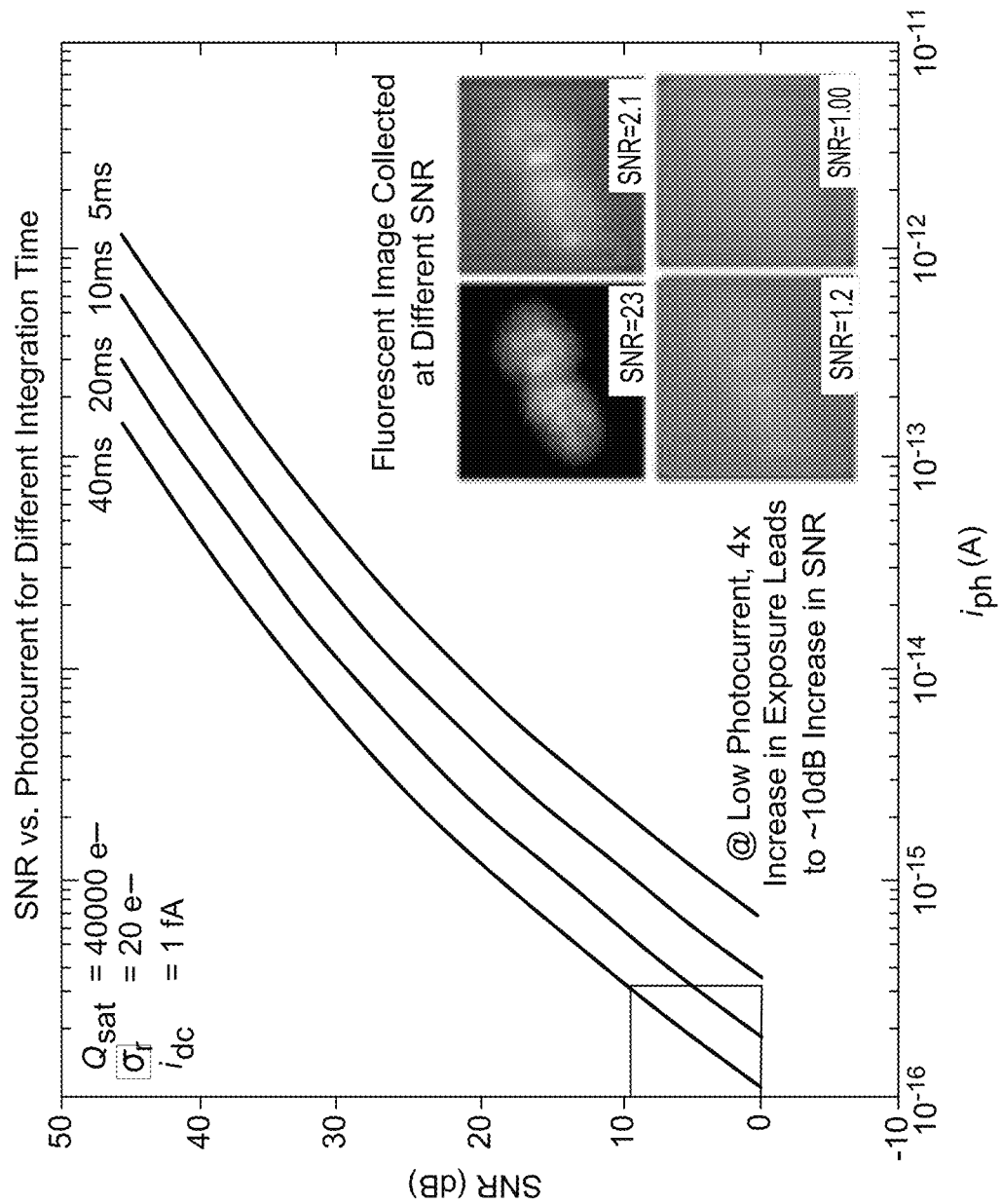
FIG. 8B shows the relationship between signal-to-noise ratio (SNR) and photocurrent at different exposure time.

FIG. 8A shows dominant noise source at different photocurrent. FIG. 8B shows the relationship between signal-to-noise ratio (SNR) and photocurrent at different exposure time. As described herein, the PCE technique can prolong the pixel exposure to enhance the SNR of the sampled videos, while relying on sparse reconstruction algorithm to recover the videos and reduce motion blurring. This technique can generate tremendous benefits for low-light imaging, where the sensor SNR is dominated by the pixel's circuit's readout noise. FIGS. 8A and 8B illustrate the relationship of SNR versus photocurrent and outline the dominant noise source at different illumination intensities. More importantly, in conventional imaging techniques, a sizable fraction of time pixels can be insensitive to emitted photons, i.e. these photons are completely wasted. In the technique described herein, the pixels are collecting photons in the same amount as with a traditional CIS with global shutter.

In CMOS sensors, the pixel readout noise is usually a type of thermal noise with a flat frequency response. The power of this thermal noise depends on temperature and is independent of the signal power. Therefore, the signal power can be enhanced by increasing the pixel exposure time to improve the overall sensor SNR. FIG. 8B shows the relationship of SNR versus photocurrent at different exposure time. It can be seen that at low light conditions, a 4× increase in exposure time can result in 10 dB of SNR improvement.

For static scenes, the exposure time of a sensor may be prolonged to improve the SNR. For dynamic scenes, however, sampling prolonging the exposure time can limit the sensor's frame rate and result in motion blurring. This challenge can be addressed by the PCT technique and the sampling pattern 600 described herein. Using coded and prolonged exposures, each pixel receives the benefits of enhanced SNR. Sparse reconstruction methods are then employed to recover low blurring video frames. The result is a low motion blur video with enhanced SNR. For fluorescent imaging applications, this technique can result in higher detectability of cells and their activities under single-photon and two-photon illumination.

The sampling pattern 600 can also have the benefit of preventing photobleaching by decreasing illumination source power compared to traditional CIS imaging. Under uniform illuminations, one can use prolonged coded exposure to improve the sensor SNR. On the other hand, prolonged exposure can also maintain the same sensor SNR under reduced illumination power. This is can be beneficial for fluorescent imaging applications due the photobleaching effects.

Figure 9A:
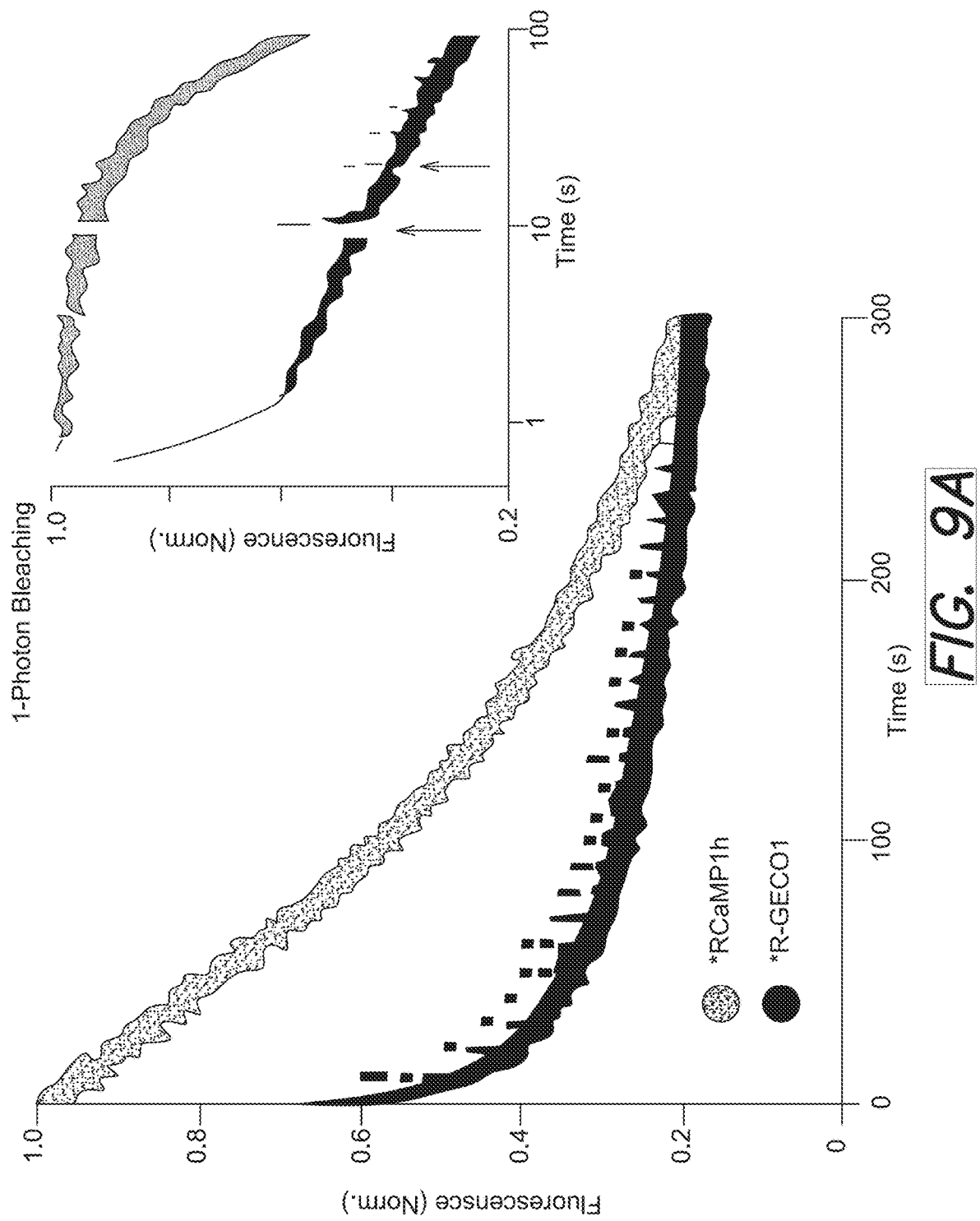
FIG. 9A shows photobleaching of fluorescent indicators over time under 1-photon illumination over time.
Figure 9B:
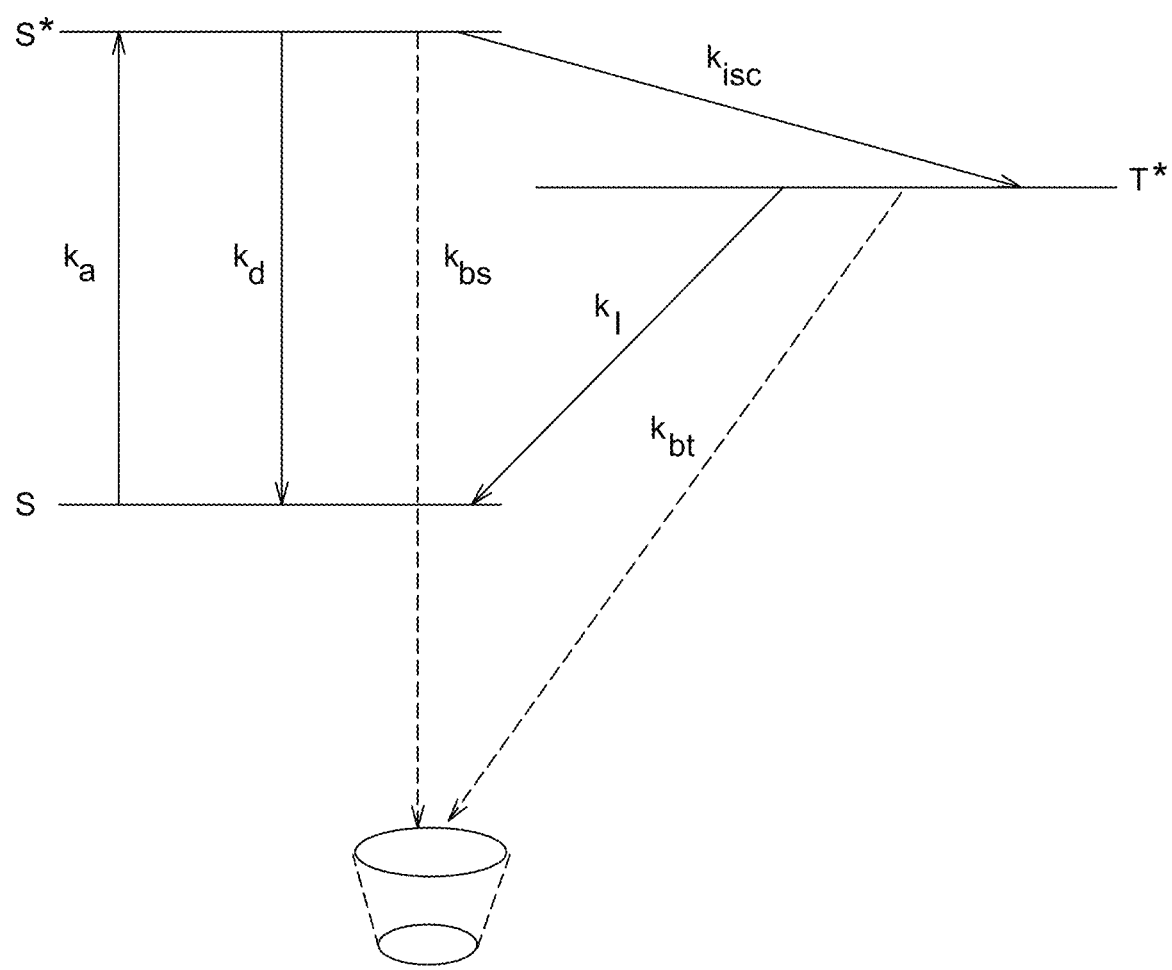
FIG. 9B illustrates the photobleaching mechanism.

FIG. 9A shows photobleaching of fluorescent indicators over time under 1-photon illumination over time. FIG. 9B illustrates the photobleaching mechanism. Without being bound by any particular theory or mode of operation, photobleaching refers to the irreversible destruction of a fluorophore that can occur when the fluorophore is in an excited state under direct illumination. Photobleaching can lead to the fading of fluorescence over time during operation, as illustrated in FIG. 9A. Depending on the fluorescent indicator, a typical experiment may last around 20 minutes to about 30 minutes before the fluorescent signals degrade below a threshold SNR. This sets the upper time limits to an experiment per day per animal, after which the animal must be rested to allow cells to produce additional fluorophores.

As illustrated in FIG. 9B, with excitation energy, a fluorophore can enter excited singlet state with a rate of $K_a$, after which the fluorophore has a chance enter the triplet state ($K_{isc}$). Photobleaching can occur at both the excited singlet and triple state with rates of $K_{bs}$ and $K_{bt}$, respectively. Therefore, on the first order, the photobleaching effects can be linearly related to the excitation energy, governed by these constant rates.

Figure 10:
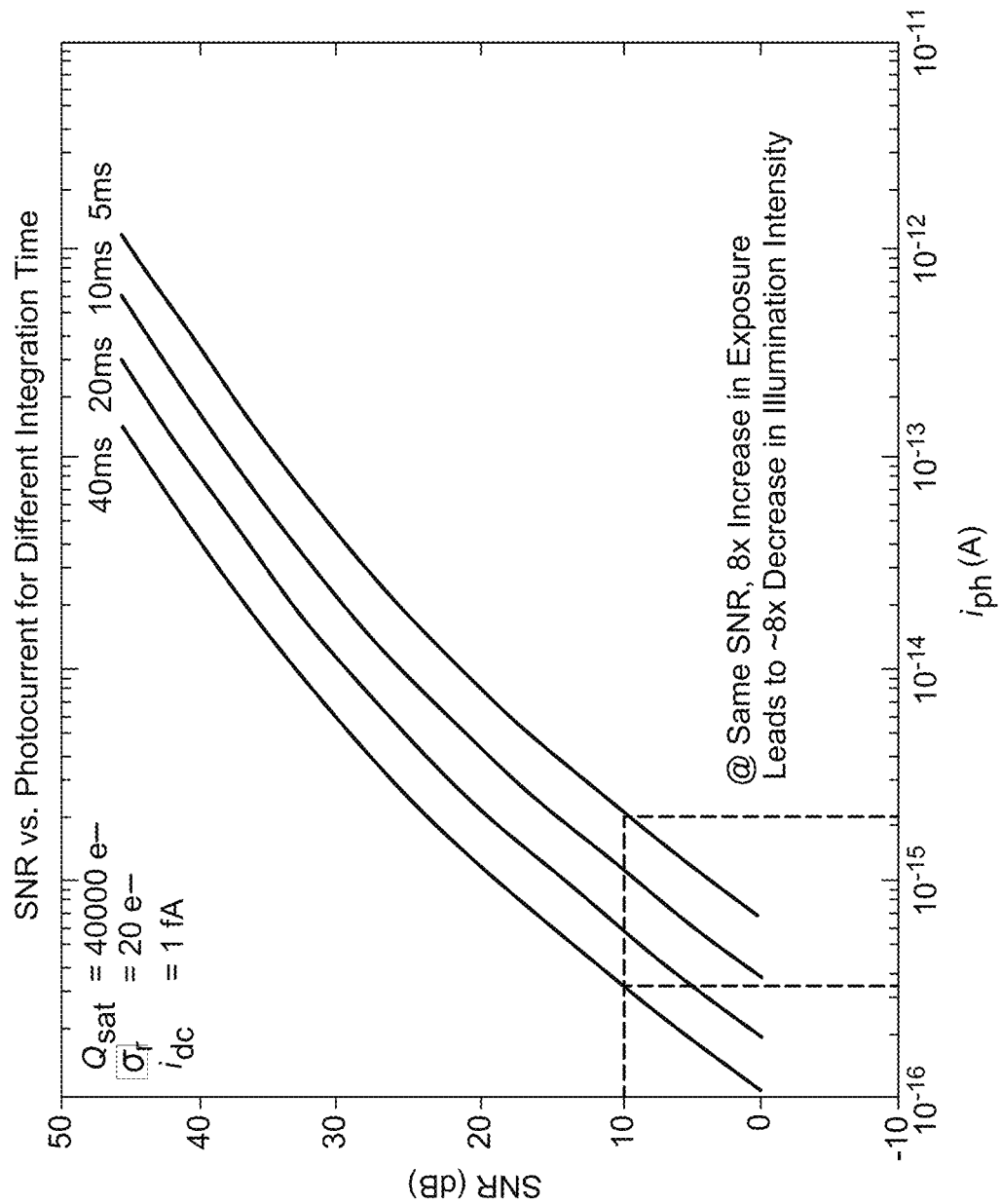
FIG. 10 shows calculated SNR as a function of illumination intensities at different exposure time.

FIG. 10 shows calculated SNR as a function of illumination intensities at different exposure time. To prevent photobleaching, experimenters typically use the lowest illumination setting while maintaining acceptable SNR and temporal resolution. The CS-PCE technique described herein offers a solution to prolong the experiment time by using even lower illumination. As illustrated in FIG. 10, maintaining the SNR at 10 dB, a 40 ms exposure can guarantee this at $10^{-15.8}$ A of photocurrent. A 5 ms exposure can guarantee this at $10^{-14.9}$ A of photocurrent.

As discussed herein, photocurrent is direct proportional to illumination intensity. Therefore, for a fixed SNR, an 8× increase in exposure time can lead to about 8× decrease in illumination intensity. As FIG. 9B shows, the excitation rate and photobleaching rate are govern by constants. Therefore, an 8× decrease in illumination intensity can reduce photobleaching by the same amount, thereby improving experiment time also by about 8 times. Such improvement can allow neuroscientists to use functional fluorescent imaging to study brain mechanism that requires longer experimental time. Some examples are learning tasks where animals are required to run multiple sessions of tasks during a single day.

On-chip Exposure Memory and Interface

Using the apparatus 200 shown in FIG. 2A as pixels, a sensor chip can be constructed with precise and simple control of the EX signal achieved using off-pixel memories. FIG. 11 shows a schematic of a sensor chip 1100 including a pixel array 1110. Each pixel 1115 in the pixel array 1110 can be substantially similar to the apparatus 200 shown in FIG. 2A. The sensor chip 1110 also includes a memory element 1130 that is operably coupled to the pixel array 1110 via a memory interface 1120. A pseudo-random generator 1140 is employed to generate the exposure control bits that are then loaded into the memory element 1130. In some examples, the pseudo-random generator 1140 can include two 7-bit Linear Feedback Shift registers (LFSRs) per row to generate a pseudo random sequence containing the row positions to start and end exposure.

Figure 11:
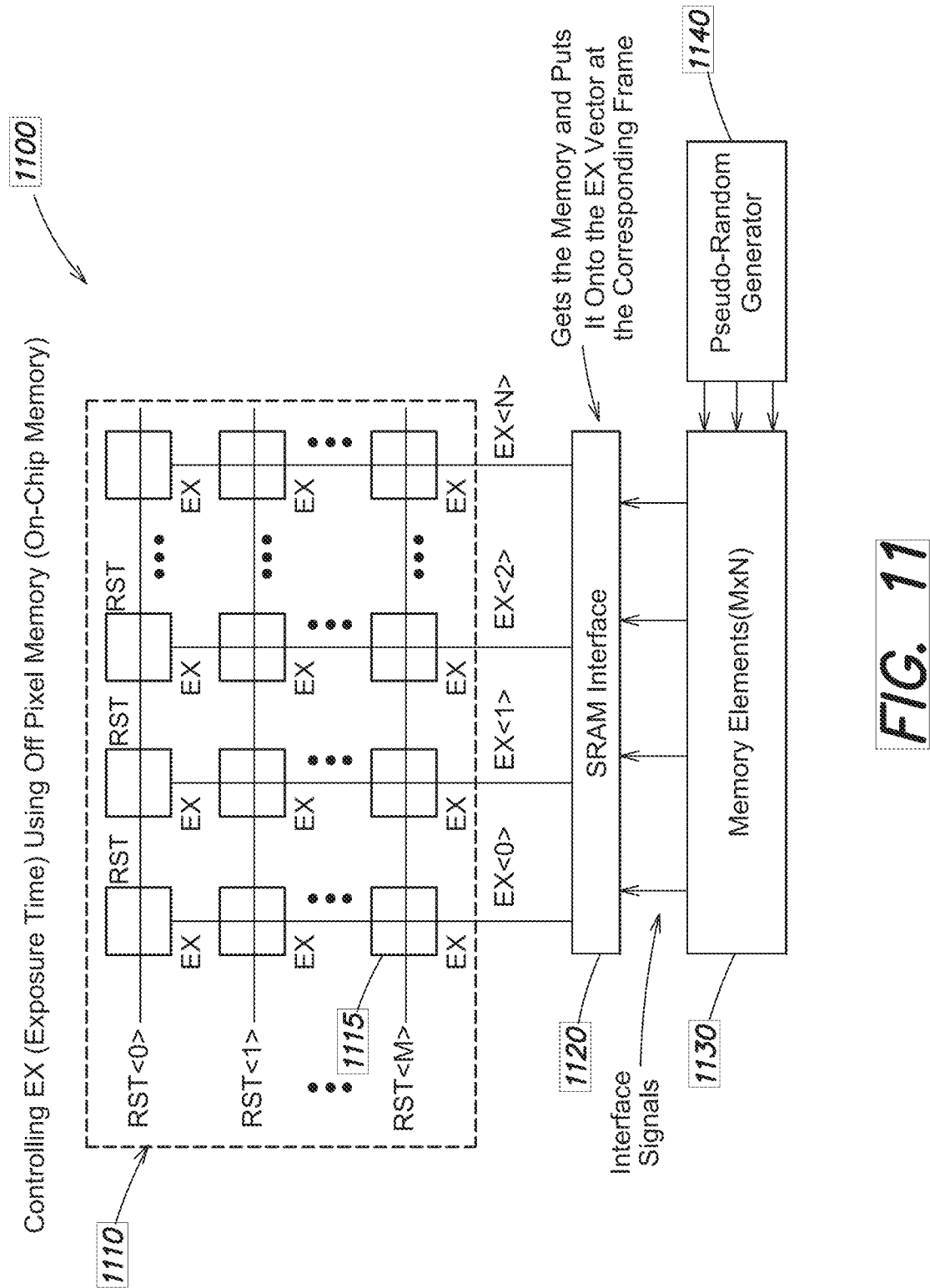
FIG. 11 shows a schematic of [ ].

As shown in FIG. 11, the pixel array 1110 has M rows and N columns. Accordingly, there are N EX signals numbered EX<0> to EX<N−1>, and M RST signals numbered from RST<0> to RST<N−1>. The pixels in a column have their EX signal connected together. The pixels in a row have their RST signals connected together. The memory element 1130 contains M×N memory elements corresponding to the size of the pixel array 1110. During operation, the SRAM interface 1120 reads from the corresponding row of the memory element 1130 and drive the EX signals.

PCE Implemented with Other Types of Detectors and Pixel Structures

Figure 12:
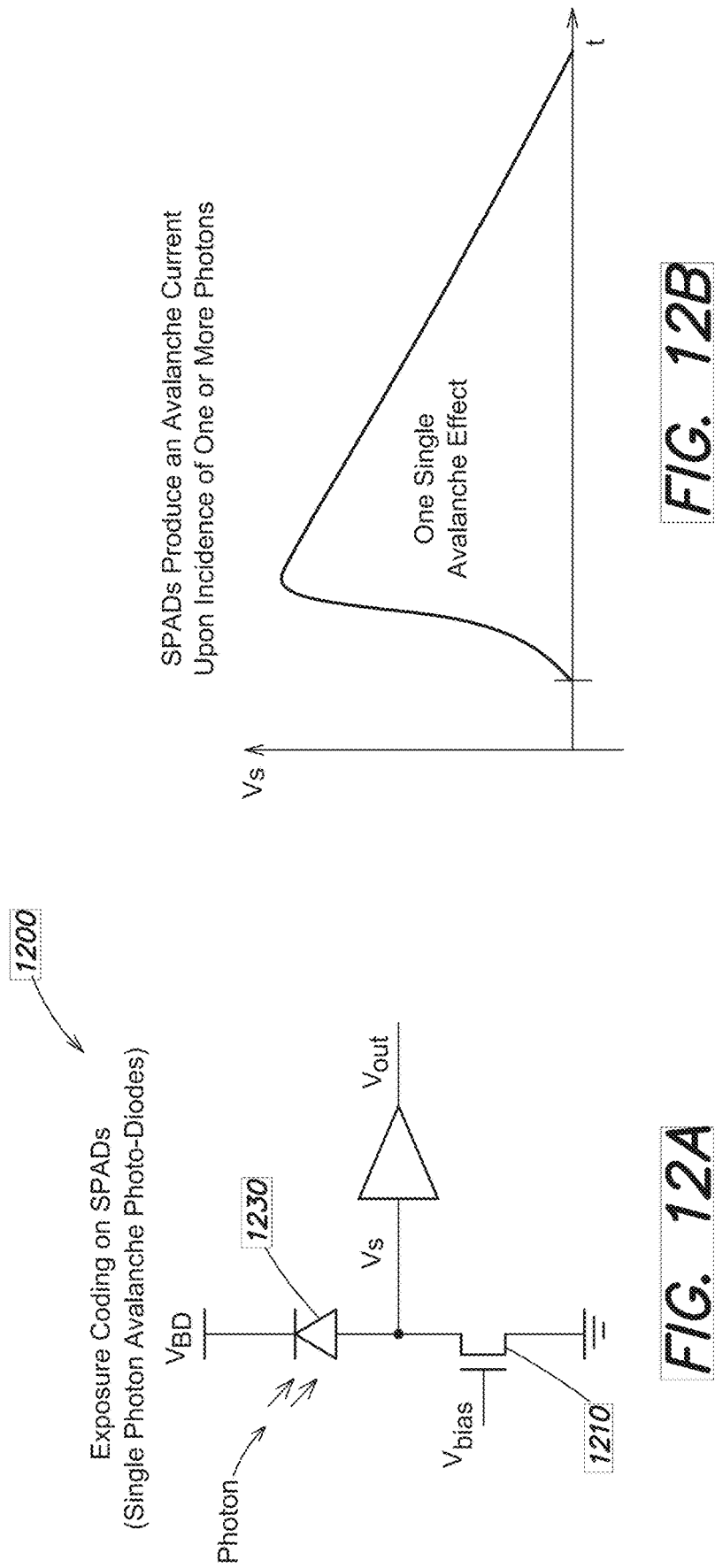
FIG. 12A shows a schematic of a single-phone avalanche diodes (SPAD) that can be used as the detector in the apparatus shown in FIG. 2A.
FIG. 12B illustrates the mechanism of avalanche effect.

Pixel wise coded exposure can be applied to other types of photo-diode based pixels. For example, FIG. 12A shows a schematic of a single-phone avalanche diodes (SPAD) 1200 that can be used as the detector 210 in the apparatus 200 shown in FIG. 2A. The SPAD 1200 includes a diode 1230 electrically coupled to a transistor 1210 that can apply a bias voltage on the diode 1230. In general, the SPAD 1200 can include an inverter or a buffer that converts the avalanche pulse into a digital pulse. In addition, SPAD pixels can operate without amplifiers because SPAD itself is using the avalanche effect to amplify the photocurrent.

During operation, when the diode 1230 is biased near the breakdown voltage, a single or multiple photons hitting the diode 1230 may initiate an avalanche effect that produces a large amount of current, as illustrated in FIG. 12B. SPADs have been used for time-of-flight application and can be used for biomedical imaging applications as well due to its single-photon sensitivity.

Since SPAD essentially converts intensity information into events in time, there is also a probability of a photon generating an avalanche effects. Therefore, counting the number of event, or counting the time between two events, can provide indications of intensity. As a result, exposure control can be applied at the level of the counters placed after SPAD diodes. This feature can be especially useful for imaging in the ultra-low light regime, where only tens to hundreds of photons are emitted per module per second.

Figure 13:
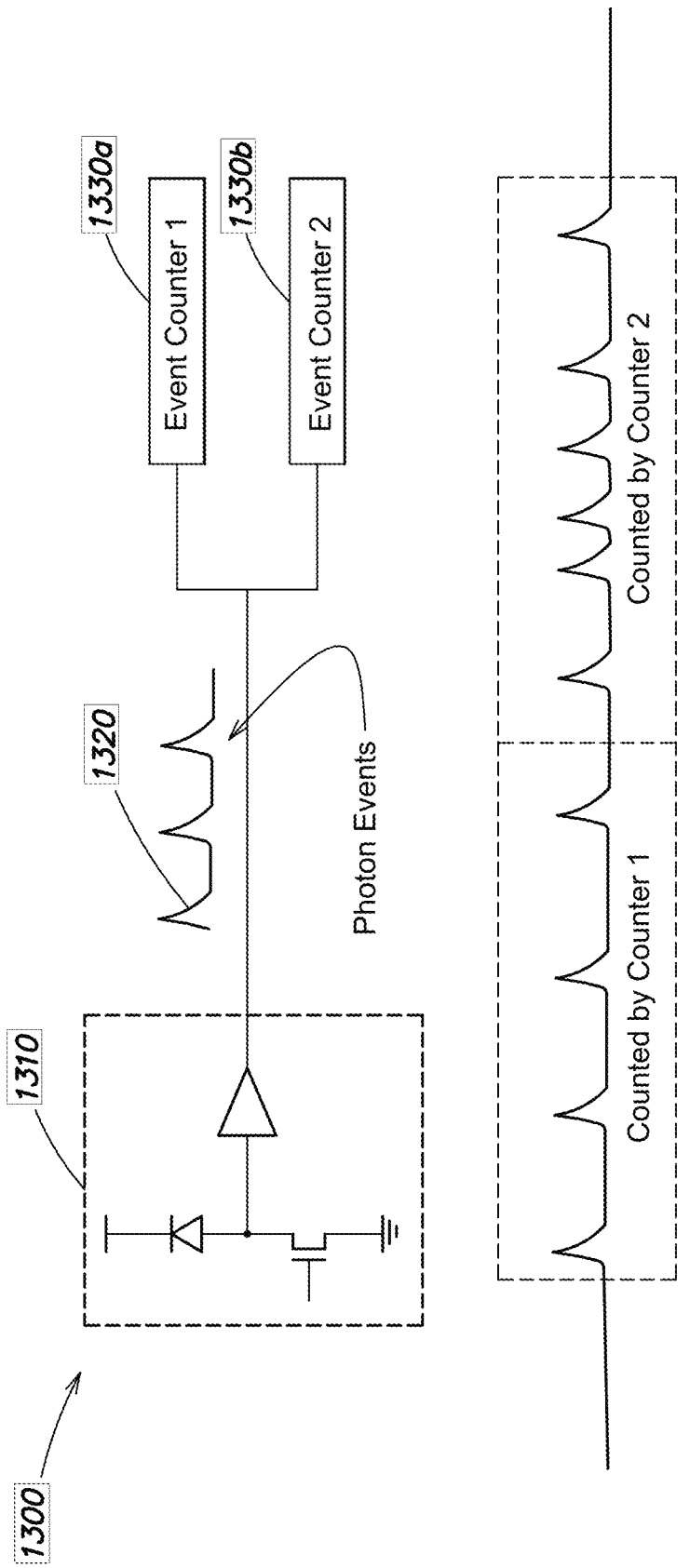
FIG. 13 shows a schematic of a system using SPAD to implement CS-PCE.

FIG. 13 shows a schematic of a system 1300 using SPAD to implement CS-PCE. The system 1300 includes an SPAD 1310 configured to produce an output signal 1320 including a train of peaks 1320, each of which corresponds to an avalanche event that is initiated by an incident photon. The output signal 1320 is measured by two event counters 1330a and 1330b. The system 1300 can be employed to conduct the coded exposure since one event counter (e.g. 1330a) can be read while the other event counter (e.g., 1330b) can be sampled. In addition, the two counters 1330a and 1330b can be switched at random times for each pixel in order to implemented PCE. This architecture can make sure that the system 1300 is always taking measurement of the detected photons.

Figure 14:
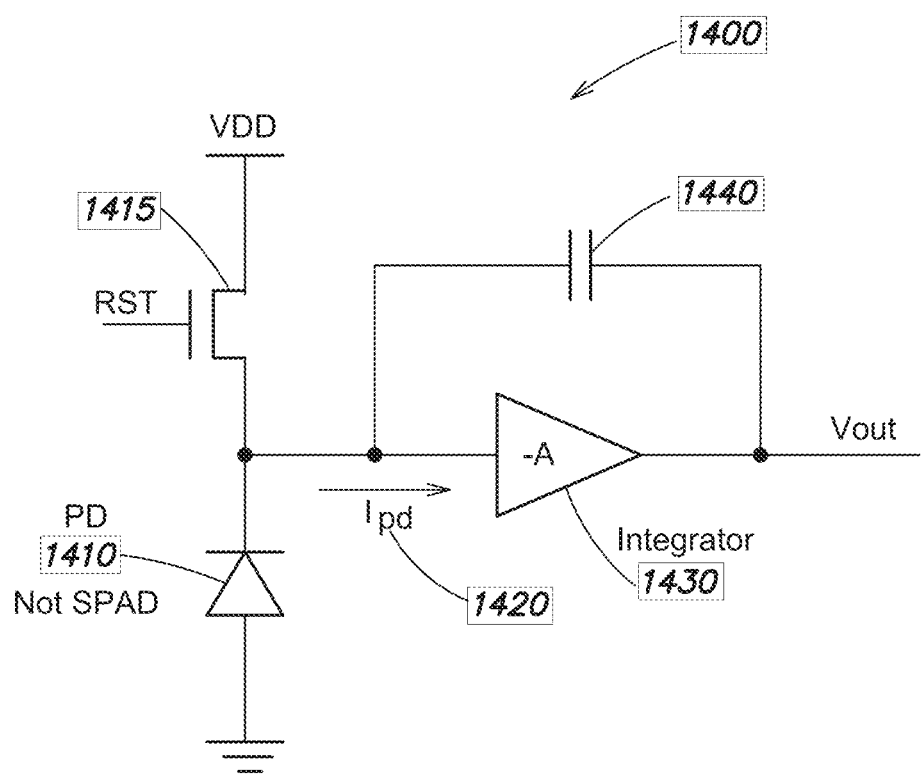
FIG. 14 shows a schematic of an event based pixel to implement CS-PCE.

FIG. 14 shows a schematic of an event based pixel 1400 to implement CS-PCE. The pixel 1400 includes a photodiode 1410 operably coupled to a transistor 1415 configured to apply a bias voltage on the photodiode 1410. Photocurrent 1420 ("$I_{pd}$") generated by the photodiode 1410 is sent to an integrator 1430 that can integrate the photocurrent 1420 onto a capacitor 1440.

The event based pixel 1400 uses a regular photo-diode 1410 as the photo sensitive element. Instead of measuring the photodiode voltage, the event based pixel 1400 integrates the photo-current 1420 onto the capacitor 1440. Once the voltage on the capacitor 1440 is greater than a pre-set threshold, the pixel generates an event. Similar to SPAD based pixels shown in FIG. 13, intensity information here is also encoded in the number of events or the time between two events. More information can be found in: Culurciello, E., Etienne-Cummings, and R., & Boahen, K. A. (2003), A biomorphic digital image sensor. *IEEE Journal of Solid-State Circuits*, 38(2), 281-294, (2003), which is incorporated by reference in its entirety. Similar to the system 1300 shown in FIG. 13, controlling the on and off time of the event counter can apply exposure control techniques to the pixel 1400.

CS-PCE Implemented in Biological Applications

The CS-PCE technique described herein can be applied in at least two categories of biological imaging. The first category is "functional" fluorescent microscopy using wide-field illumination, and the second category includes both static and "functional" scanning fluorescent microscopy.

"Functional" Fluorescent Microscopy Using Wide-Field Illumination

Without being bound by any particular theory or mode of operation, functional fluorescence refers to the fluorescence where the fluorescent intensity has both a spatial and a temporal dynamic that depends on a biological process. In one example, functional fluorescence can have temporal dynamics of biological signaling processes, such as intracellular calcium activity levels (popular in neural imaging) or a voltage-sensitive protein embedded in a nerve cell's membrane. In another example, functional fluorescence can be found in motions of an organism, organ, single cell, or sub-cellular component over time due to motor activity (e.g., larval fish swimming, C-elegans motion) or developmental processes (e.g., mitosis). Wide-field usually refers to the situation where the whole imaging plane is illuminated with light that excites fluorophores in the specimen, and frames are captured by a CCD or CMOS sensor array.

In functional fluorescent microscopy, pixels like the apparatus 200 shown in FIG. 2A or pixel array like the system 1100 shown in FIG. 11 can be used for imaging via the CS-PCE technique. There are at least two advantages of using PCE and sparse reconstruction in functional fluorescent microscopy.

First, spatiotemporal dynamics (i.e. movie) of the scene (e.g., 2D imaging plane or 3D imaging volume) can be reconstructed with high fidelity (e.g., similar to normal wide-field imaging). However, the PCE technique allows much longer individual pixel exposure times while maintaining temporal fidelity. This means that the illumination intensity can be decreased in inverse proportion to the increased pixel exposure time. The reduced illumination intensity, in turn, reduces photo-bleaching, which is the photochemical alteration of a fluorophore molecule such that the fluorophore permanently loses its ability to fluoresce. Aside from rendering the fluorescent molecule useless for imaging, this process can have deleterious effects on the health of biological tissue.

Second, although the excitation intensity and the per-pixel exposure time may be similar to those in conventional wide-field illumination case, application of random start and stop times during PCE allows the resolution of temporal dynamics to be much faster than the coded image rate. In other words, the PCT technique can be used to resolve temporal dynamics (e.g. those of voltage sensitive dyes and proteins) that are difficult or impossible to resolve with traditional image sensors.

Existing wide-field imaging devices can also be improved by incorporating the PCE technique described herein. Image sensor used by these existing wide-field imaging devices can be improved by incorporating the PCE techniques described herein. One benefit of this incorporation is that PCE sensor provides a performance advantages on low light and high speed sensing applications. These wide-field imaging device can incorporate PCE by replacing the image sensor, which all the other components remain unchanged. These devices include, for example, microendoscope imaging systems for recording neural activity (e.g. those produced by Inscopix), light-sheet scanning systems for recording neural and motor activity as well as small specimen motion (e.g., those produced by Ziess, Olympus, Nikon, and Leica, etc.), and high-speed standard wide field fluorescent microscopes (e.g. Ziess, Olympus, Nikon, etc.) for functional imaging that currently rely on specialty, high-speed scientific CMOS cameras.

Static and "Functional" Scanning Fluorescent Microscopy

Figure 15A:
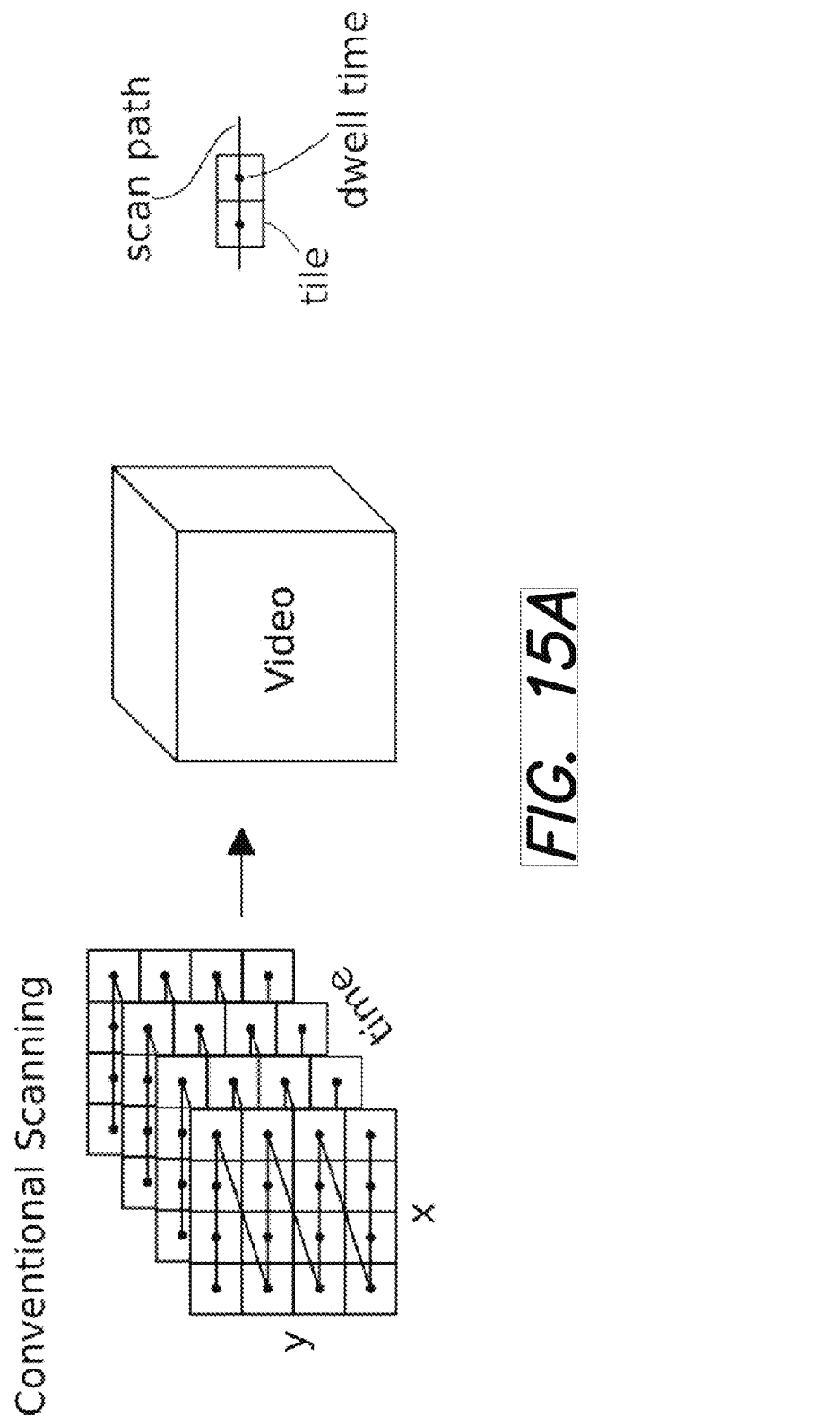
FIGS. 15A and 15B illustrate the procedures of conventional scanning microscopy and coded scanning microscopy via CS-PCE, respectively.
Figure 15B:
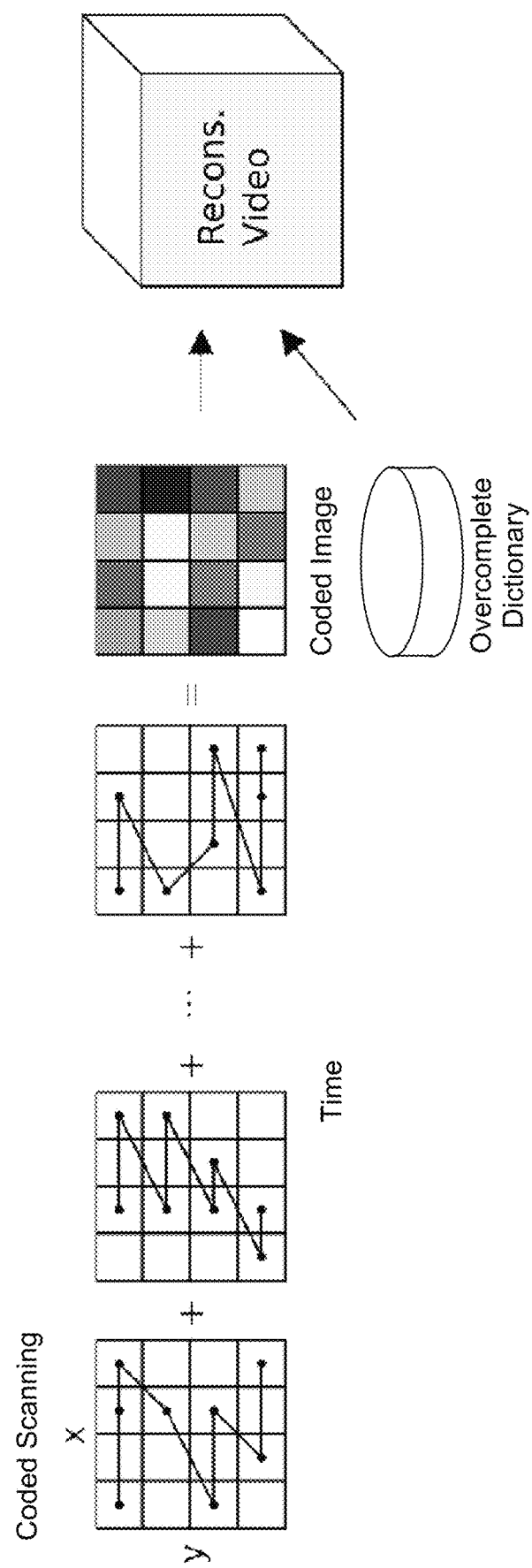

FIGS. 15A and 15B illustrate the procedures of conventional scanning and coded scanning, respectively. As used herein, "static" refers to a situation where the scene is fixed and the fluorescent intensity does not change as a function of time. Fluorescent intensity is only a function of space. "Scanning" refers to the situation where one point of imaging volume is illuminated per unit time using a light source (e.g., a laser). The light source is moved position by position across the entire imaging volume. At each point, the light source stays for a pre-specified amount of time (the "dwell time"). The light emitted/reflected by the point on the sample is collected by a photomultiplier tube (PMT) or photon counting device and is used to build an image of the volume, as illustrated in FIG. 15A.

In contrast, a pixel-wise motion coded exposure image can be created using existing scanning hardware by randomly skipping scanning positions. In other words, the scanned points can be a random subset of the total points that are otherwise scanned in conventional scanning microscopy. After the scanning, the same sparse reconstruction principles used for images produced by the integrated sensor can be used to reconstruct 3D (two spatial and one temporal dimension) or 4D (three spatial and one temporal dimension) movies, as illustrated in FIG. 15B. Additionally, since this PCT technique allows for selective excitation of arbitrary positions in 3D space, sub-sampled data of static scenes can be reconstructed to form a full image. This means that the PCT technique can have advantages for both functional and static imaging.

There are several advantages of applying the CS-PCE technique in scanning microscopy. First, the scanning speed can be increased. Because only a fraction of the tiles within a scanning volume are visited, scanning speed increases approximately in proportion to the fraction of skipped tiles. Second, the data rate can be reduced. Because only a fraction of the tiles within scanning volume need to be saved, the data rate can be decreased. Third, in low-light imaging, the dwell time at each point can be increased. Because only a fraction of the tiles within a scanning volume are visited, the dwell time can be increased to improve SNR while maintaining scan speed for weak fluorescent signals during functional imaging applications. Fourth, the PCT technique can decrease photobleaching. In the case where dwell time is maintained compared to conventional scanning, but only a fraction of tiles is visited, the average photobleaching rate of the specimen can be reduced in proportion to the fraction of scanned tiles since the photobleaching rate is in general linearly proportional to the excitation power.

Existing scanning imaging devices can also be improved using the PCE technique described herein. The first example is confocal imaging systems (e.g., produced by Ziess, Olympus, Nikon, Leica, etc.). Confocal microscopy is a standard technique for collecting high-quality images of fixed specimens. Photobleaching benefits can be profound in confocal imaging because confocal imaging does not control out-of-plane excitation. Even though imaging may be well localized to a single z-slice, the out-of-plane volume is continuously bombarded with high energy light. Photobleaching is a limiting factor in the usefulness of this technique currently. As discussed herein, using the PCE technique can effectively reduce the photobleaching effect. The advantage of a coded scan is that it can decrease the number of scans to reconstruct an image. This is advantageous for two-photon microscopy where the speed of the system is usually limited by the scan time per frame. Using coded scan described here can sub-sample the spatial-temporal field of view and increase the frame rate of scanning microscopy techniques.

The second example can be the 2-photon imaging systems (e.g., produced by Ziess, Olympus, Nikon, and Leica, etc.). 2-photon imaging is a standard technique for collecting high-quality images of fixed specimens and for functional imaging. Two-photon imaging does not produce out-of-plane excitation and therefore causes much less photobleaching compared to confocal imaging. Functional 2-photon imaging can benefit from the PCE technique because the scanning speed can be increased (as discussed above). The increased scanning speed, in turn, would allow imaging of biological processes with faster temporal dynamics. The increased scanning speed can also allow larger scan volumes while maintaining reconstructed frame rates.

CS-PCE Implemented in Genetically Encoded Voltage Indicators (GEVIs)

Genetically encoded calcium indicators (GECIs) are routinely used to read out the intracellular calcium level of mammalian neurons, which is used as a proxy for spiking activity, in hundreds of cells simultaneously. This has led to several breakthroughs in the understanding of dendritic computation, place field formation, and cortical microcircuit self-organization. However, intracellular calcium dynamics are usually slow. For example, a single spike results in a $Ca^{2+}$ impulse that is about 50 ms to about 100 ms. Therefore, it can be challenging to resolve fast temporal spiking patterns, regardless of the GECI's speed. For this reason, developing a genetically encoded voltage indicator (GEVI) with adequate speed, membrane localization, and brightness to report action potentials in mammalian cells has been a major goal in neuroscience for the past two decades.

Despite much effort towards creating genetically encoded fluorescent voltage sensors, none have yet achieved widespread adoption. In general, opsin-based fluorescent reporters are relatively dim and suffer from poor membrane localization, whereas GFP-based fluorescent reporters exhibit small changes in fluorescence, photobleach rapidly, and spectrally overlap with optogenetic controllers. On example of opsin-based fluorescent voltage reporter is called Archon, which exhibits good localization in neurons of multiple species, several fold improved brightness over previous opsin-based reporters, order-of-magnitude improvements in voltage sensitivity and photobleaching over GFP-like reporters, and compatibility with optogenetic control. Archon can robustly report sub-millisecond timescale readout of the membrane voltage and outperforms existing molecules in terms of stability, membrane localization, and action potential detectability. For example, Archon exhibits high sensitivity in intact brain circuits, with a 20% change in fluorescence and an excellent signal-to-noise ratio of 30 to 40 for action potentials in mouse cortical tissue.

Even with these improvements, the desired imaging speed and localization to the cell membrane of Archon still presents major challenges for high-speed imaging. For example, the fast frame rates lead to very short photon integration times of signals that are weak to begin with. Currently, even single neuron GEVI imaging involves a state of the art, low noise sCMOS device to meet sample-rate and signal-to-noise (SNR) requirements for action potential detection. These devices are usually large, power-hungry, bandwidth intensive, and only support a limited field of view (FOV) at maximal frame rate. Accordingly, it is challenging to integrate these systems into head-mountable devices in freely moving mammals and capture spikes from large numbers of cells simultaneously.

Without being bound by any particular theory or mode of operation, the Shannon/Nyquist sampling theorem indicates that video must be acquired at two times the maximal spatial and temporal signal bandwidth in order to prevent aliasing and measurement error. This criterion is overly conservative for biological microscopy where signals are statistically sparse and therefore amenable to compressive sensing (CS) techniques.

One approach to implement CS techniques can use a CMOS image sensor with pixel-wise exposure ("CS-PCE Camera") to leverage CS for high-speed imaging (e.g., apparatus 200 shown in FIG. 2A). As described above, the CS-PCE camera allows independent exposure of each pixel on the sensor array, instead of globally exposing the array in lock-step with a frame clock. This individual exposure allows frame-rate-independent photon integration time, compressive sampling, and accurate reconstruction of high speed video from code frames acquired at sub-Nyquist frame rates.

The CS technique can be implemented in imaging GEVI, where a 1000 FPS video of Archon readout of action potentials can be accurately reconstructed from a CS-PCE camera operated at 100 FPS (i.e. corresponding to 10× compression rate). Additionally, using frame rate independent pixel-wise exposure and slow readout can save power, vastly reduce system size, and increase SNR while maintaining action potential detectability compared to sCMOS devices operated at 1000 frames per second (FPS). This opens the door to a head-mountable GEVI imaging microscope.

In some examples, the system implementing the CS-PCE technique can be configured as a head-mountable miniature microscope (miniscope) capable of direct spiking readout from large, Archon-expressing neural populations in freely moving mammals. This system can provide a genetically-targetable replacement multiple-single unit electrophysiology techniques in many use cases. For validation, the system is used to directly image hippocampal place cell sequence replay in freely moving mice, which is currently only possible multiple single unit electrical recordings.

Direct optical readout of the neuronal membrane voltage confers many advantages compared to electrical recording: genetic targetability, increased subject throughput, increased cell yield, report of axonal- and dendritically-localized features of neural activity, and reduced tissue invasiveness. The systems described herein can be a transformative technical advance because they can provide a true replacement for microelectrode-based recordings in many use cases, which has been a long sought after goal for systems neuroscience research.

Archerhodopsin-Based Genetically Encoded Fluorescent Voltage Reporter

Until very recently, GEVIs have suffered from poor membrane targeting, temporal stability, sensitivity, and low signal-to-noise characteristics. The optogenetic silencer Archaerhodopsin (Arch) usually exhibits a voltage dependent fluorescence but the excitation intensities are usually very strong, thereby precluding in-vivo use. To address this drawback, Archaerhodopsin can be modified into a new form, called Archon, using directed evolution techniques. Archon can be used with reduced excitation intensities and is a potent reporter of the neuron membrane potential. Archon (so named because it is based on Arch, with 13 point mutations) also exhibits good performance along multiple parameter dimensions desired in a fluorescent voltage reporter: good localization, high SNR, large and linear fluorescent changes, high speed of response, photobleaching improved by 1-2 orders of magnitude versus earlier reporters, and full compatibility with optogenetic control. Archon, therefore, represents a practical fluorescent voltage reporter that may find widespread use in neuroscience.

Integrated CS-PCE Camera for In-Vivo GEVI Imaging

The CS-PCE described herein is a low power, all-CMOS integrated version of temporal compressive sensing with pixel-wise coded exposure to acquire fluorescent signals from biological tissue. Because compressive sensing capabilities are supplied on-chip, the size of the device can be equivalent to a conventional CMOS imaging sensors and can be integrated into existing head-mounted miniature microscopes to image Archon in freely moving animals.

Practical Evaluation of the CS-PCE Miniscope in Freely Moving Mice

Place cells were one of the first targets of head-mountable calcium imaging microscopes because of their broad scientific interest to the neuroscience community and major limitations of tetrode-based recordings in terms of long-term stability. Hippocampal place cells can be used as a testing ground for two novel uses of the CS-PCE miniscope, including: (1) high frame-rate direct fluorescent voltage readout of place cell replay sequences; and (2) streaming, wireless calcium imaging of place cell activity during exploration.

GEVI-based optical imaging can allow direct readout of temporally compressed action potential sequences that are challenging to capture with conventional head-mounted microscopes. Hippocampal replay sequence recording is currently only observable using microelectrodes due to their high speed. Direct optical readout would provide a definitive and scientifically meaningful validation of the CS-PCE miniscope for in-vivo voltage imaging. Independently, wireless, streaming calcium imaging enables major improvements in the ethological relevance of behavioral tasks that can be performed during imaging. For example, it will become possible to image during outdoor foraging, many-animal social interaction, and burrowing through enclosed 3D environments.

Preliminary Characterizations: CS-PCE on Existing GEVI Recordings

The preliminary characterizations of CS-PCE GEVI imaging employed high-speed videos of a neuron expressing Archon. Raw GEVI video, acquired at 1000 FPS, was collected with a high-speed sCMOS camera (Zyla 5.5; Andor Technology). The video is split into a testing and training dataset, the latter of which was used to train an over-complete dictionary for sparse reconstruction. Finally, CS-PCE was simulated by compressing every 10 frames into a single coded image with pixel exposure (NTe=3 ms). This preliminary result shows that even using a non-optimal training dictionary, and working with pre-digitized image sequences rather than true fluorescent signals, PCE accurately reconstructs the voltage amplitude time series at a 10× compression rate. Action potential timing and shape are accurately reconstructed. This provides strong evidence that PCE can be used for accurate high-speed imaging of GEVIs while vastly reducing system size, bandwidth, and power requirements.

Implement a CS-PCE Sensor for GEVI Imaging

The CS-PCE technique can be implemented using a CS-PCE sensor that supports a faster frame rate (1000 FPS) and a larger FOV (512×512 pixels). This sensor can be manufactured in a CMOS image sensor fabrication process which provides high sensitivity and low noise photodiode and pixel readout transistors. Some commercial process foundry candidates include X-fab 180 nm CIS process and the TowerJazz 180 nm CIS process.

The silicon architecture of the sensor can use row scan column readout timing. In-pixel memory values are updated one row at a time at maximum rate of 1000 FPS, while the ADC samples the pixel array at maximum of 200 FPS. This allows any compression rate greater than 5. The pixel-wise random exposure pattern can be generated on-chip using pseudo-random generator (see, e.g., FIG. 11). The compression rate and the exposure length can be user configurable. To reduce external circuitry for inter-chip communication on the headstage, the chip I/O can interface directly to a serializer (e.g., the Texas Instrument DS90UB913A serializer). The serializer bundles data and power into a high-speed stream to transmit over a coaxial cable. The chip can be integrated into standard benchtop epifluorsence microscope and used to image neurons in cultured networks and brain slices that express Archon.

Wireless Mini-Microscope for Compressive GCaMP Imaging

A head mounted fluorescent mini-microscope can be constructed using the CS-PCE sensor described herein. This device can allow extremely low power acquisition of GECI's in-vivo and enable the first miniscope with streaming wireless transmission. Additionally, it can also allow to develop best practices for reconstruction of coded frames from CS-PCE cameras used for functional fluorescence imaging in-vivo against ground truth data acquired using tried and true acquisition methods.

In the wireless CS-PCE miniscope for GCaMP Imaging, the optical and mechanical architecture of the miniscope can be similar to existing devices (e.g., the open-source UCLA miniscope). In terms of interface electronics, the sensor can include a low power, ultra-wideband (UWB) radio, so the complexity and weight of interface electronics can be reduced. The host interface can be implemented using off-the-self FPGA development boards (e.g., from Opal-Kelly) and an existing custom wireless transceiver module. With an expected compression rate greater than 10, a 30 FPS video can be reconstructed with less than 3 FPS sampling rate. This reduction in data allows the utilization of streaming wireless transmission for long experiments using a small lithium polymer battery.

Mini-Microscope for GEVI Imaging

In this CS-PCE miniscope for GEVI imaging, which can be a combination of the CS-PCE sensor and the mini-microscope described above, Archon can be excited by a 637 nm red laser, with emission gated by a 660 long-pass filter. To explore a full range of excitation intensities, 10-500 mW/mm$^2$ light irradiance can be delivered to the brain. These ranges are often used in optogenetic neural control of the mammalian cortex. Therefore, the onboard excitation LED can be replaced with an optical fiber to deliver light from an inexpensive red laser (637 nm, Coherent, OBIS 637LX, Pigtailed). A coaxial tether can be used to interface the sensor with the rest of the system so as to transmit video at about 100 Hz to achieve 1000 FPS reconstructed videos.

In GEVI imaging using CS-PCE, it might be challenging for the pixels to meet performance specifications for conversion gain, quantum efficiency, and read noise to guarantee detectability of the GEVI in vivo. This challenge may be addressed through exhaustive modeling. For example, the GEVI response can be first simulated using existing MATLAB models so as to determine the pixel specification to guarantee optimal detectability. With knowledge of the target specification, the pixel can be simulated using foundry-provided models over multiple design corners so as to choose the appropriate pixel architecture that satisfies the target specification.

The CS-PCE technique specifically addresses SNR and contrast issues associated with conventional CMOS cameras. However, in densely labeled tissue using volumetric excitation, it can be difficult to assign detected florescent light to particular cells. To deal with this issue, expression of Archon can be sparsified until individual cells can be resolved. In the cell layer of CA1, even 1% labeling will provide even 1% labeling can provide a large number of cells that can be imaged simultaneously within a single FOV.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
   an array of pixels, at least a first pixel in the array of pixels comprising:
      a first detector to generate a first electrical signal in response to irradiation by incident radiation;
      a first transistor electrically coupled to the first detector;
      at least one logic gate to implement a Boolean AND logic function, the at least one logic gate comprising:
         a first input terminal to receive a first exposure signal;
         a second input terminal to receive a first reset signal; and
         an output terminal, electrically coupled to the first transistor, to output to the first transistor a first control signal to variably control a first variable exposure time of the first detector and to reset the first detector; and
   a random generator, operably coupled to the first input terminal of the at least one logic gate, to generate the first exposure signal.

2. The apparatus of claim 1, wherein the first detector comprises a photodiode.

3. The apparatus of claim 1, wherein the first detector comprises a single-photon detector.

4. The apparatus of claim 1, wherein the first pixel further comprises:
   memory operably coupled to the first input terminal of the at least one logic gate, the memory storing information representing the first variable exposure time.

5. The apparatus of claim 4, wherein the memory comprises a one-bit static random-access memory (SRAM).

6. The apparatus of claim 1, wherein the array of pixels comprises M rows of pixels and N columns of pixels, and the apparatus further comprises:
   memory operably coupled to the array of pixels, the memory storing a plurality of exposure signals including the first exposure signal; and
   a memory interface, operably coupled to the memory and the array of pixels, to transmit an ith exposure signal of the plurality of exposure signals to an ith column of the N columns of pixels, where i=1, 2, . . . N.

7. The apparatus of claim 1,
   wherein the first control signal controls the first detector, based at least in part on the first exposure signal, to generate:
   at least a first portion of a first frame of image using a first random exposure time, and
   a second portion of a second frame of image using a second random exposure time different from the first random exposure time.

8. The apparatus of claim 1, wherein each pixel in the array of pixels comprises a corresponding detector and a corresponding logic gate implementing the Boolean AND logic function, the corresponding logic gate comprising:
   a first corresponding input terminal to receive a corresponding exposure signal;
   a second corresponding input terminal to receive a corresponding reset signal; and
   a corresponding output terminal, electrically coupled to the corresponding detector, to output a corresponding control signal to variably control a corresponding variable exposure time of the corresponding detector and to reset the corresponding detector.

9. The apparatus of claim 8, wherein the random generator is further configured to:
   generate a first plurality of exposure signals so as to control a first random group of pixels in the array of pixels for exposure at a first timing point, and
   generate a second plurality of exposure signals so as to control a second random group of pixels in the array of pixels for exposure at a second timing point.

10. A method of compressive sensing using an array of pixels, each pixel in the array of pixels including a detector and at least one logic gate implementing a Boolean AND function and having a first input terminal, a second input terminal, and an output terminal electrically coupled to the detector, the method comprising, for each pixel of at least a first group of pixels in the array of pixels:
   sending an exposure signal, generated by a random generator, to the first input terminal of the at least one logic gate;
   sending a reset signal to the second input terminal of the at least one logic gate; and
   generating an electrical signal representative of a scene, in response to irradiation of the detector by incident photons emitted from the scene, based on an output signal of the at least one logic gate, the output signal variably controlling a variable exposure time of the detector and resetting the detector.

11. The method of claim 10, wherein the scene includes biological tissue.

12. The method of claim 11, wherein:
the irradiation of the detector by incident photons emitted from the scene is representative of neural activities in the biological tissue, and
generating an electrical signal comprises generating the electric signal representative of the neural activities in the biological tissue.

13. The method of claim 12, further comprising:
generating the photons emitted from the scene using genetically encoded calcium indictors (GECIs) disposed in the biological tissue.

14. The method of claim 12, further comprising:
generating the photons emitted from the scene using genetically encoded voltage indicators (GEVIs) disposed in the biological tissue.

15. The method of claim 12, further comprising:
recording the electrical signal from each pixel to form an encoded image; and
reconstructing a spatio-temporal video of the neural activities based on the encoded image.

16. The method of claim 10, wherein the exposure signal comprises at least one waveform including a single exposure trigger randomly located within a predetermined time span.

17. The method of claim 16, wherein the exposure signal comprises:
a first waveform including a first single exposure randomly located at a first location within a predetermined time span; and
a second waveform including a second single exposure trigger randomly located at a second location, different from the first location, within the predetermined time span.

18. The method of claim 17, wherein the first single exposure trigger has a first width and the second single exposure trigger has a second width different from the first width.

19. The method of claim 10, wherein the exposure signal comprises at least one waveform including multiple exposure triggers distributed within a predetermined time space so as to generate multiple encoded images.

20. An apparatus for compressive sensing, the apparatus comprising:
an array of pixels comprising M rows of pixels and N columns of pixels, each pixel in the array of pixels comprising:
a photodiode to generate an electrical signal in response to irradiation by incident radiation;
a first transistor electrically coupled to the photodiode; and
a logic gate implementing a Boolean AND logic function and comprising:
a first input terminal to receive a first exposure signal;
a second input terminal to receive a first reset signal; and
an output terminal, electrically coupled to the first transistor, to output to the first transistor a first control signal controlling a variable exposure time of the photodiode and resetting the photodiode;
memory, operably coupled to the array of pixels, to store a plurality of exposure signals including the first exposure signal;
a memory interface, operably coupled to the memory and the array of pixels, to transmit an ith exposure signal to an ith column of pixels, where i=1, 2, . . . N; and
a random generator, operably coupled to the memory, to generate the plurality of exposure signals, wherein a first exposure signal includes a first sequence of valleys distributed within a predetermined time span and a second exposure signal includes a second sequence of valleys distributed within the predetermined time span.

* * * * *